United States Patent
Collins et al.

(10) Patent No.: US 10,815,777 B2
(45) Date of Patent: Oct. 27, 2020

(54) METHOD TO DETECT INCREMENTAL OIL PRODUCTION ARISING FROM A LOW SALINITY WATERFLOOD

(71) Applicant: BP Exploration Operating Company Limited, Middlesex (GB)

(72) Inventors: Ian Ralph Collins, Middlesex (GB); John William Couves, Middlesex (GB); Michael Graham Hodges, Middlesex (GB); Christian Schack Pedersen, Copenhagen (DK); Peter Anthony Salino, Middlesex (GB); Christianne Clare Wicking, Middlesex (GB)

(73) Assignee: BP EXPLORATION OPERATING COMPANY LIMITED, Middlesex (GB)

( * ) Notice: Subject to any disclaimer, the term of this patent is extended or adjusted under 35 U.S.C. 154(b) by 205 days.

(21) Appl. No.: 16/086,662

(22) PCT Filed: Mar. 14, 2017

(86) PCT No.: PCT/EP2017/056007
§ 371 (c)(1),
(2) Date: Sep. 20, 2018

(87) PCT Pub. No.: WO2017/162489
PCT Pub. Date: Sep. 28, 2017

(65) Prior Publication Data
US 2019/0100996 A1    Apr. 4, 2019

(30) Foreign Application Priority Data
Mar. 23, 2016   (GB) .................................. 1604962.9

(51) Int. Cl.
*E21B 49/08* (2006.01)
*E21B 43/20* (2006.01)
(Continued)

(52) U.S. Cl.
CPC .............. *E21B 49/087* (2013.01); *C09K 8/58* (2013.01); *E21B 43/20* (2013.01);
(Continued)

(58) Field of Classification Search
CPC .......... G01N 33/2823; G01N 33/2835; G01N 24/081; E21B 43/20; E21B 49/0087; E21B 49/0875; C09K 8/58
See application file for complete search history.

(56) References Cited

U.S. PATENT DOCUMENTS

| 7,455,109 B2 | 11/2008 | Collins |
| 9,085,971 B2 | 7/2015 | Janssen et al. |

(Continued)

FOREIGN PATENT DOCUMENTS

| CN | 101023242 A | 8/2007 |
| CN | 103890315 A | 6/2014 |

(Continued)

OTHER PUBLICATIONS

PCT/EP2017/056007 International Search Report and Written Opinion dated May 15, 2017 (17 p.).
(Continued)

*Primary Examiner* — Natalie Huls
(74) *Attorney, Agent, or Firm* — Conley Rose, P.C.

(57) ABSTRACT

A method for detecting incremental oil production from an oil-bearing reservoir includes taking a baseline sample of the oil and analyzing the baseline sample of oil to establish a baseline compositional signature for the oxygen-containing organic compounds in the oil. In addition, the method includes commencing a low salinity waterflood by injecting
(Continued)

a low salinity water into the reservoir from an injection well. Further, the method includes recovering oil from a production well. Still further, the method includes taking post-flood samples of the oil produced from the production well over time. The method also includes analyzing the post-flood samples of oil to establish post-flood compositional signatures for the oxygen-containing organic compounds in the oil. Moreover, the method includes identifying a difference between one or more of the post-flood compositional signatures and the baseline compositional signature that is characteristic of incremental oil released by the low salinity waterflood.

17 Claims, 9 Drawing Sheets

(51) Int. Cl.
*G01N 33/28* (2006.01)
*C09K 8/58* (2006.01)
(52) U.S. Cl.
CPC ..... *G01N 33/2823* (2013.01); *G01N 33/2835* (2013.01); *E21B 49/0875* (2020.05)

(56) References Cited

U.S. PATENT DOCUMENTS

| | | | |
|---|---|---|---|
| 10,041,339 B2 | 8/2018 | Jerauld et al. | |
| 2010/0006283 A1* | 1/2010 | Collins | E21B 43/20 166/261 |
| 2012/0143579 A1* | 6/2012 | Collins | E21B 44/00 703/10 |
| 2012/0310614 A1* | 12/2012 | Beattie | C09K 8/035 703/10 |
| 2013/0125630 A1* | 5/2013 | Collins | G01N 1/00 73/64.56 |
| 2014/0290942 A1 | 10/2014 | Brodie et al. | |
| 2014/0345862 A1* | 11/2014 | Jerauld | E21B 43/16 166/275 |
| 2015/0300149 A1 | 10/2015 | Collins et al. | |
| 2016/0160621 A1* | 6/2016 | Collins | E21B 43/20 166/270.1 |
| 2017/0017011 A1* | 1/2017 | Howard | G01N 15/088 |

FOREIGN PATENT DOCUMENTS

| | | |
|---|---|---|
| CN | 104011328 A | 8/2014 |
| CN | 104334678 A | 2/2015 |
| WO | 2008/029124 A1 | 3/2008 |

OTHER PUBLICATIONS

McGuire, P.L., et al., "Low Salinity Oil Recovery: An Exciting New EOR Opportunity for Alaska's North Slope," SPE Western Regional Meeting, Irvine, California, Mar. 30, 2005 (SPE 93903) (15 p.).

Seccombe, Jim, et al., "Demonstration of Low-Salinity EOR at Interwell Scale, Endicott Field, Alaska," SPE Improved Oil Recovery Symposium, Tulsa, Oklahoma, Apr. 28, 2010 (SPE 129692) (12 p.).

Seccombe, James C., et al., "Improving Waterflood Recovery: LoSal EOR Field Evaluation," SPE/DOE Improved Oil Recovery Symposium, Tulsa, Oklahoma, Apr. 23, 2008 (SPE 113480) (17 p.).

Tang, Guo-Qing, et al., "Influence of Brine Composition and Fines Migration on Crude Oil/Brine/Rock Interactions and Oil Recovery," Journal of Petroleum Science and Engineering, vol. 24, Dec. 1, 1999, pp. 99-111 (13 p.).

Jerauld, G.R., et al., "Modeling Low-Salinity Waterflooding," SPE Annual Technical Conference and Exhibition, San Antonio, Texas, Sep. 24, 2006 (SPE 102239) (13 p.).

Chinese Office Action dated Jun. 29, 2020, for Chinese Application No. 201780032115.0 (8 p.).

\* cited by examiner

METHOD TO DETECT INCREMENTAL OIL PRODUCTION ARISING FROM A LOW SALINITY WATERFLOOD

CROSS-REFERENCE TO RELATED APPLICATIONS

This application is a 35 U.S.C. § 371 national stage application of PCT/EP2017/056007 filed Mar. 14, 2017 and entitled "Method to Detect Incremental Oil Production Arising from a Low Salinity Waterflood," which claims priority to GB Application No. 1604962.9 filed Mar. 23, 2016 and entitled "Method to Detect Incremental Oil Production Arising from a Low Salinity Waterflood," both of which are hereby incorporated herein by reference in their entirety for all purposes.

STATEMENT REGARDING FEDERALLY SPONSORED RESEARCH OR DEVELOPMENT

Not applicable.

BACKGROUND

The present invention relates to monitoring a low salinity waterflood in an oil reservoir.

In the first stage of hydrocarbon recovery from a reservoir (referred to as "primary recovery"), natural pressure in the reservoir forces hydrocarbon fluids towards a production well where the fluids can flow or can be pumped to a surface production facility. Primary recovery may be continued where the reservoir pressure is above the oil bubble point pressure. If the reservoir pressure falls below the oil bubble point pressure, additional pressure support is required to prevent gas from coming out of solution in the reservoir. Generally, reservoir pressure is sufficient to recover only around 10 to 20 percent of the total oil present in a subterranean reservoir. Accordingly "secondary recovery" techniques are applied to recover oil from reservoirs in which the hydrocarbon fluids no longer flow by natural forces.

Waterflooding is one of the most successful and extensively used secondary recovery methods. Water is typically injected, under pressure, into reservoir rocks via injection wells to maintain the reservoir pressure and to sweep the oil through the reservoir rock towards production wells. The water used in waterflooding may be a high salinity water, for example, seawater, estuarine water, aquifer water, or produced water (water separated from oil and gas at a production facility).

The water used in waterflooding may also be a low salinity water. Thus, International Patent Application No. WO/2008/029124 teaches that oil recovery from a reservoir comprising an oil-bearing sandstone rock formation is enhanced (in comparison with injection of a high salinity water) when the injection water has a total dissolved solids (TDS) content in the range of 200 to 12,000 ppmv and the ratio of the multivalent cation content of the injection water to that of the connate water contained within the sandstone rock is less than 1.

The increase in the amount of oil that can be recovered from sandstone reservoirs by lowering the salinity of the injected water has been demonstrated on a laboratory scale (Tang, G.-Q., and Morrow, N. R., 1999, "Influence of brine composition and fines migration on crude oil/brine/rock interactions and oil recovery", Journal of Petroleum Science and Engineering), using single well tracer tests (McGuire, P. L., Chatham, J. R., Paskvan, F. K., Sommer, D. M., and Carini, F. H., 2005, "Low Salinity Oil Recovery: An Exciting New EOR Opportunity for Alaska's North Slope", SPE 93903) and using full scale field trials (Seccombe, J., Lager, A., Jerauld, G., Jhaveri, B., Buikema, T., Bassler, S., Denis, J., Webb, K., Cockin, A., and Fueg, E., 2010, "Demonstration of Low-Salinity EOR at Interwell Scale, Endicott Field, Alaska", SPE 129692).

Knowledge of oil and water saturation is crucial to mature field management. Saturation changes within the reservoir are an indication of how the oil reservoir is swept by an injection water and how much oil is released from the reservoir rock. However, tracking of saturation changes in an oil reservoir does not, by itself, provide information concerning the production of incremental oil arising from a low salinity flood.

A method for determining the amount of incremental of oil that is produced with a low salinity waterflood in comparison with the amount of oil that would be produced using a high salinity waterflood, such as a seawater flood, is important for better management of a low salinity waterflood. This is particularly important where a low salinity waterflood is carried out in secondary recovery mode, either at commencement of oil recovery from the reservoir or after primary recovery under the natural pressure of the reservoir, because there is no baseline high salinity waterflood from which to determine the incremental oil recovery.

SUMMARY

According to a first aspect of the present invention, there is provided a method for detecting incremental oil production from an oil-bearing reservoir that is penetrated by at least one injection well and at least one production well, the process comprising:

taking a baseline sample of the oil and analyzing the baseline sample of oil to establish a baseline compositional signature for the oxygen-containing organic compounds in the oil;

commencing a low salinity waterflood by injecting a low salinity water into the reservoir from the injection well;

recovering oil from the production well;

taking post-flood samples of the oil produced from the production well over time;

analyzing the post-flood samples of oil to establish post-flood compositional signatures for the oxygen-containing organic compounds in the oil; and identifying a difference between one or more of the post-flood compositional signatures for the oxygen-containing organic compounds in the oil and the baseline compositional signature for the oxygen-containing organic compounds in the oil that is characteristic of incremental oil released by the low salinity waterflood.

By identifying a difference between one or more of the post-flood compositional signatures for the oxygen-containing organic compounds in the oil and the baseline compositional signature for the oxygen-containing organic compounds in the oil, it is possible to detect if incremental oil is being released during a low salinity waterflood. The method provides the means to gain valuable information relating to the arrival of incremental oil at a production well.

According to a second aspect of the present invention, there is provided a method for detecting incremental oil production from an oil-bearing reservoir comprised of a plurality of layers of reservoir rock wherein the reservoir is penetrated by at least one injection well, at least one production well and at least one surveillance well located between the injection well and production well, the process comprising:

introducing logging equipment into the surveillance well;

injecting a low salinity water into the reservoir from the injection well and recovering oil from the production well;

utilizing the logging equipment over time to determine the period of time, $t_1$, between commencing injection of low salinity water into the reservoir from the injection well(s) and the detection of the front of the low salinity water at the surveillance well;

determining the interwell distance, $L_1$, between the injection well(s) and surveillance well, and calculating the velocity, v, at which the front of the low salinity water advances through the reservoir wherein $v=L_1/t_1$;

determining the interwell distance, $L_2$, between the surveillance well and production well(s) and using the frontal advance velocity, v, to predict the time, t2, at which the low salinity water breaks through into the production well wherein $t_2=t_1+L_2/v$;

taking a baseline sample of oil from the reservoir and analyzing the baseline sample of oil to establish a baseline compositional signature for the oxygen-containing organic compounds in the oil;

taking post-flood samples of the oil produced from the production well(s) over time and analyzing the samples of oil to establish post-flood compositional signatures for the oxygen-containing organic compounds in the oil to identify a difference between one or more of the post-flood compositional signatures for the oxygen-containing organic compounds in the oil and the baseline compositional signature for the oxygen-containing organic compounds in the oil that is characteristic of incremental oil released by the low salinity waterflood;

increasing the frequency at which post-flood samples of the produced oil are taken as the time approaches the predicted time, $t_2$, at which low salinity injection water breaks through into the production well and using the identified difference between the post-flood and baseline composition signatures for the oxygen-containing organic compounds in the oil to determine the time at which incremental oil breaks through into the production well.

By using a surveillance well to determine the time at which low salinity injection water breaks through into the production well, post-flood samples of oil can be more effectively taken as the time approaches the predicted time. This may, for example, reduce the requirement of taking unnecessary samples.

Further features and advantages of the invention will become apparent from the following description of preferred embodiments of the invention, given by way of example only, which is made with reference to the accompanying drawings.

DEFINITIONS

Throughout the following description the following terms are referred to:

"Incremental oil" is the additional oil that is recovered using a low salinity injection water over a conventional high salinity injection water.

"Baseline sample of oil" is a sample of "moveable oil". The term "moveable oil" is well known to the person skilled in the art and refers to oil that is naturally moveable in a reservoir.

"Post-flood sample of oil" is a sample of oil taken after commencing injection of a low salinity water into an injection well.

"Compositional signature for the oxygen-containing organic compounds" is the relative abundance of one or more of the oxygen-containing organic compounds in the oil.

"High Resolution Mass Spectrometry (HRMS)" is a mass spectrometric analytical technique that produces spectra of the mass-to-charge (m/z) values of ionisable compounds to an accuracy of four decimal places.

"Bank of oil" is well known to the person skilled in the art and refers to a portion of the reservoir where the oil saturation is increased because of the application of an enhanced oil recovery process that targets immobile oil.

"Low salinity water" is water having a total dissolved solids (TDS) in the range of 200 to 12,000 parts per million on a weight by volume basis (ppmv), preferably, 500 to 10,000 ppmv, more preferably, 500 to 5,000 ppmv, in particular, 500 to 2000 ppmv, and having a multivalent cation content less than the multivalent cation content of the connate water of the reservoir. The unit "ppmv" corresponds to the unit "mg/l". The person skilled in the art will understand that the low salinity water is of low ionic strength, for example, has an ionic strength of less than 0.15 mol/l, in particular, less than 0.1 mol/l.

"High salinity water" is water having a salinity of at least 15,000 ppmv, preferably, at least 20,000 ppmv, more preferably, at least 30,000 ppmv, in particular, a salinity in the range of 30,000 to 350,000 ppmv. The high salinity water may be seawater, estuarine water, a saline brackish water, a saline produced water, a saline aquifer water or a mixture thereof.

"Secondary waterflood" is a waterflood that occurs either after recovering oil from the reservoir under the natural pressure of the reservoir (referred to as "primary recovery") or at commencement of oil recovery from the reservoir (omitting primary recovery).

"Tertiary low salinity waterflood" is a low salinity waterflood that follows a secondary waterflood with a high salinity water.

DETAILED DESCRIPTION

Figure 1:
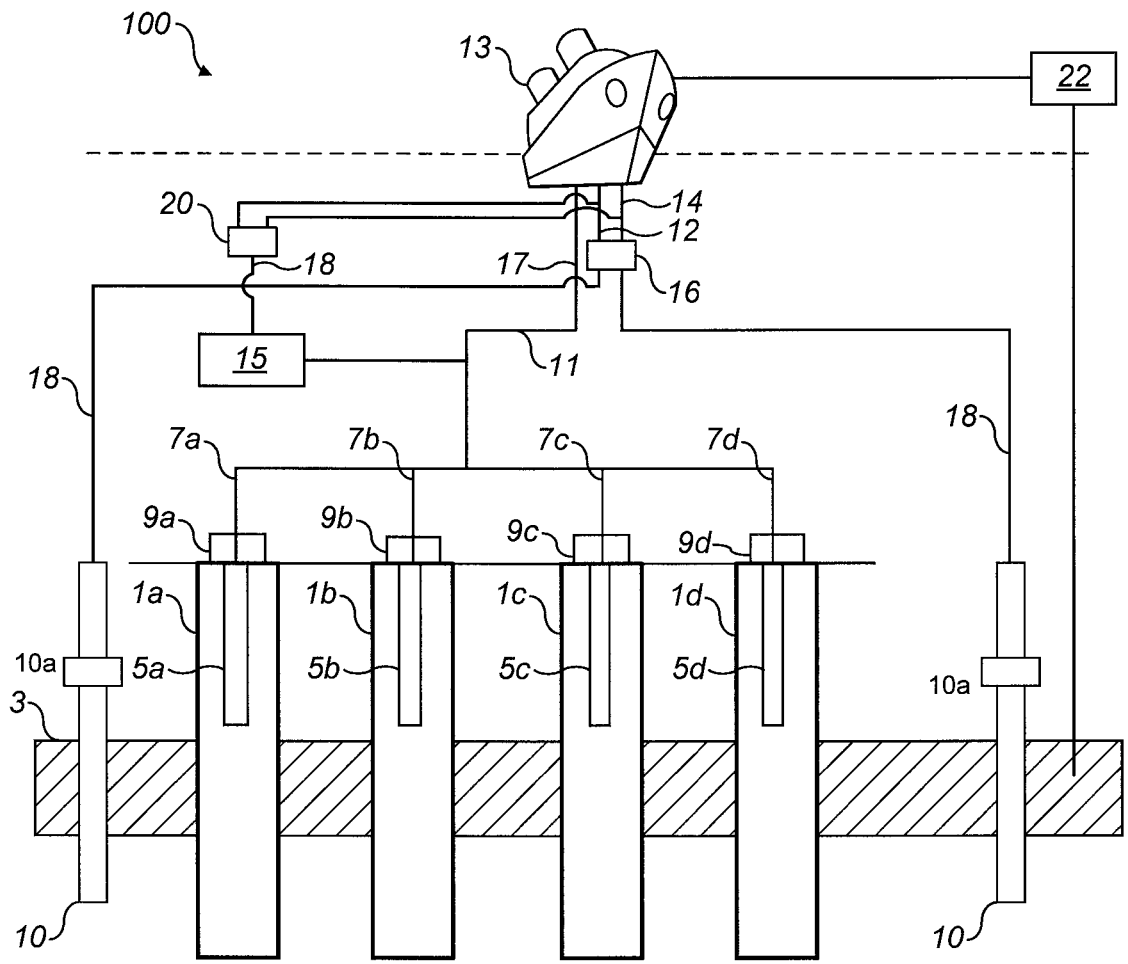
FIG. 1 is a schematic diagram showing a crude oil displacement system which is configurable in conjunction with embodiments of the invention.

FIG. 1 is a schematic block diagram showing a simplified representation of a crude oil recovery system 100 for an offshore oil field. In this Figure, a plurality of production wells 1a to 1d is used to recover oil from at least one rock formation making up an oil reservoir 3. Each production well 1a, 1b, 1c, 1d has a production tubing 5a, 5b, 5c, 5d arranged therein and is provided with a wellhead 9a, 9b, 9c, 9d, respectively. Accordingly, the production tubing of each production well serves to transport fluids, including crude oil, produced from the reservoir 3 to the wellhead. From the wellhead 9a, 9b, 9c, 9d the produced fluids pass into a flow line 7a, 7b, 7c, 7d which extend to a manifold 8 which connects the flow lines with a main flow line 11 which transfers the produced fluids to a production facility 13 located on a platform or floating production, storage and offloading installation (FPSO) via riser 17. Moreover, an additional oil reservoir (either single or multiple oil reservoirs, each reservoir having a plurality of production wells), such as generally shown by means of part 15, may be joined to the main flow line 11. The crude oil recovery system 100 also includes at least one, preferably, a plurality of injection wells 10 for injecting an aqueous displacement fluid (injection water) into the rock formation of oil reservoir 3 (similarly, the additional oil reservoir(s) of part 15 are each provided with at least one injection well, preferably, a plurality of injection wells). A first main injection line 12 for a pressurised high salinity water (such as seawater or a produced water that is separated from the crude oil at the production facility 13) and a second main injection line 14 for a pressurised low salinity water (produced using desalination equipment located on the platform or FPSO) extend from the production facility 13 to a subsea manifold 16 for reservoir 3. In some crude oil recovery systems there is one main injection line that can be used for low and high salinity water. Dedicated injection line(s) 18 extend from the subsea manifold 16 to the injection well(s) for reservoir 3. Moreover, the first and second main injection lines 12, 14 may lead to one or more additional manifold(s) 20 for each of the additional oil reservoir(s) of part 15. A controller (not shown) is provided for operating valves of the manifold(s) 16, 20 such that the dedicated injection lines(s) 18 can be switched between receiving pressurised low salinity water and pressurised high salinity water.

Although FIG. 1 shows the well heads 9a, 9b, 9c, 9d of the production wells 1a, 1b, 1c, 1d located on the seabed, in shallow waters, the production tubing may be in fluid communication with wellheads located on a platform. Similarly, the injection tubing of the injection well(s) 10 may be in fluid communication with a well head located on the platform. Accordingly, there would be no requirement for subsea flow lines 7a-7d or manifold 8.

Each reservoir 3 comprises at least one rock formation, which is porous and permeable, such as sandstone.

A crude oil displacement system of the recovery system 100 generally comprises equipment arranged to inject an aqueous displacement fluid (injection water), such as sea water or a low salinity water, into the one or more crude oil-bearing reservoirs 3. For example, the displacement system typically comprises one or more aqueous displacement fluid injection wells 10 (as shown in FIG. 1), one or more injection lines for the aqueous displacement fluid, and a controller arranged to control the injection of the aqueous displacement fluid. The displacement system may also comprise equipment associated with the treatment of the aqueous displacement fluid in preparation for injection, such as desalination equipment.

Although the crude oil recovery system 100 of FIG. 1 is for an offshore oil field, the present invention may also be used with a crude oil recovery system for an onshore oil field.

The aqueous displacement fluid is injected by injection equipment of the crude oil displacement system into the injection well(s) 10 thereof. The aqueous displacement fluid then passes through the rock formation in which crude oil and formation water are present, resulting in displacement of the crude oil from a pore space of the rock formation. The oil can then be swept through the formation to a production well 1a to 1d spaced from the injection well 10, from which it is recovered.

By identifying changes to the compositional signature of chemical components of the oil produced from a production well 1a-1d, it is possible to detect if incremental oil is being released during a low salinity waterflood. This is because certain changes in the compositional signature of the oil are indicative of incremental oil. This invention therefore provides the means to gain valuable information relating to the arrival of incremental oil at a production well 1a-1d. Optionally, it is also possible to detect the breakthrough of low salinity water into a production well 1a-1d during a low salinity waterflood.

Figure 2:
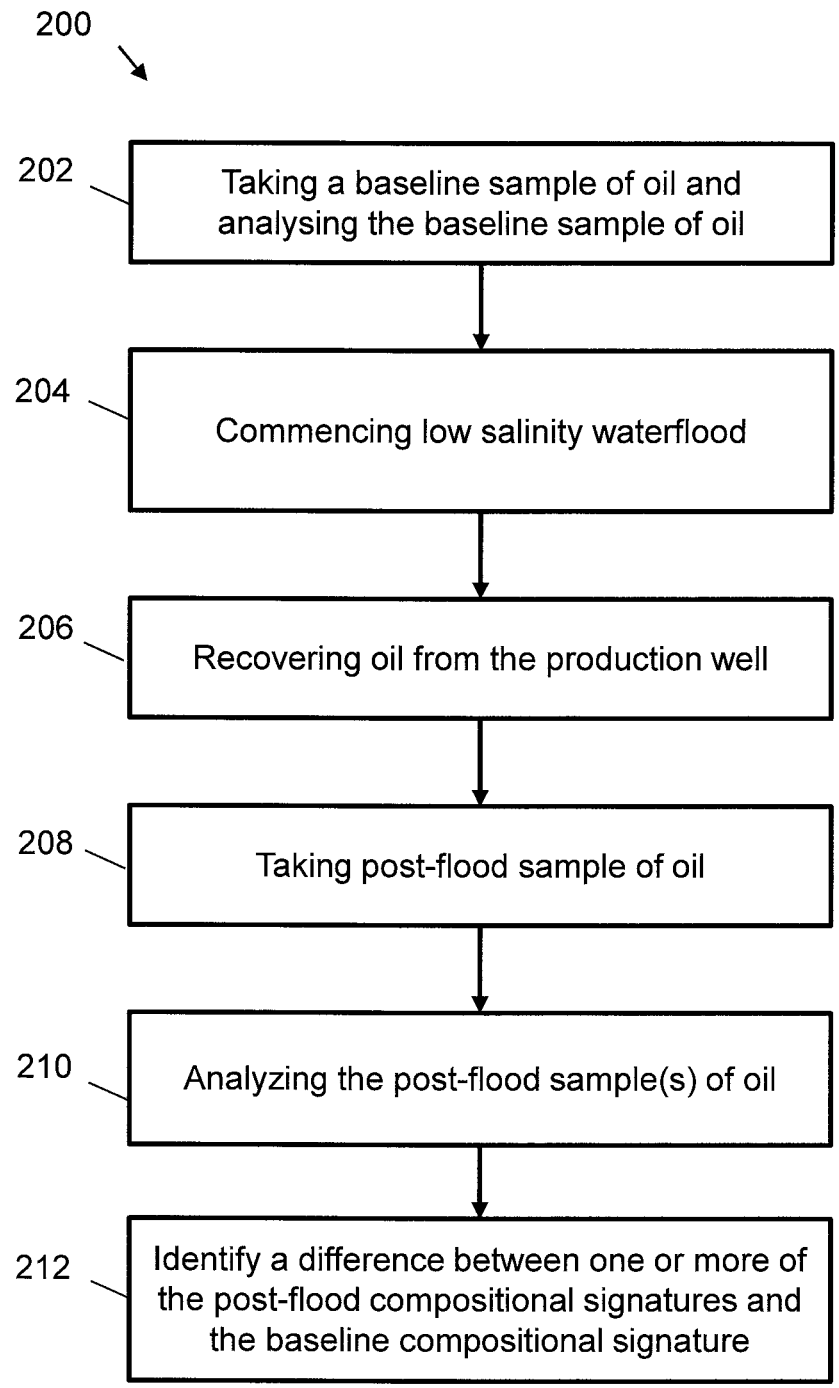
FIG. 2 is a flow diagram showing a method for detecting incremental oil production from an oil-bearing reservoir.

Accordingly, FIG. 2 provides a method 200 for detecting incremental oil production from an oil-bearing reservoir 3 that is penetrated by at least one injection well 10 and at least one production well 1a-1d. In step 202, the method comprises taking a baseline sample of the oil and analyzing the baseline sample of oil to establish a baseline compositional signature for the oxygen-containing organic compounds in the oil. The baseline compositional signature may be established in a variety of suitable ways, as discussed in more detail below.

A plurality of baseline samples of the moveable oil may be taken to establish a consistent baseline compositional signature for the oxygen-containing organic compounds in the moveable oil. For example, an average, such as arithmetic mean, baseline compositional signature may be calculated. It is envisaged that one or more of these baseline samples of moveable oil may be discarded in the event of contamination of the oil sample with, for example, drilling fluids or completion fluids used during drilling and completion of the production well 1a-1d. It may therefore be preferred to take the baseline sample of oil several days or weeks after commencement of production of oil from the production well 1a-1d.

In the case of a tertiary low salinity waterflood, the baseline sample of moveable oil may be recovered from the reservoir 3 during primary recovery, during a conventional waterflood with a high salinity water such as seawater, or may be a post-flood sample of oil taken from a region of the reservoir that is yet to be swept by the injected low salinity water.

In the case of a secondary low salinity waterflood, the baseline sample of moveable oil may be recovered from the reservoir 3 during primary recovery (unless omitted) or may be a post-flood sample of oil taken from a region of reservoir that is yet to be swept by the injected low salinity water. For example, the post-flood sample of oil may be taken either from a region of the reservoir that has yet to be subjected to a low salinity waterflood or, in the case of an injection and production well pair, may be recovered from the production well during the initial phase of the secondary low salinity waterflood, i.e., before the front of the low salinity waterflood has advanced a significant distance through the reservoir from the injection well towards the production well.

In step 204, a low salinity waterflood commences whereby a low salinity water is injected into the reservoir 3 from the injection well 10. In step 206, fluids, including crude oil, are recovered from the production well 1a-1d. In step 208, one or more post-flood samples of produced fluids are taken from the fluids produced from the production well 1a-1d over time. Techniques for sampling produced fluids are well known to the person skilled in the art. For example, post-flood samples may be taken downhole in the production well 1a-1d, at the well head 9a-9d, from the flow line 7a-7d, or at the manifold 8. The post-flood samples of produced fluids may be pressurised samples or unpressurised samples. Typically, the post-flood samples of produced fluids are separated in a laboratory located either remotely or at the production facility. In the case of pressurised samples, the post-flood samples are separated into a gaseous phase, oil phase, and aqueous phase, and the post-flood oil samples are taken from the separated oil phase. In the case of unpressurised samples, the post-flood samples are separated into an oil phase and aqueous phase, and the post-flood oil samples are taken from the separated oil phase.

The post-flood samples of produced fluids produced from the production well 1a-1d (and hence the post-flood samples of oil) may be taken either continuously or intermittently. Where post-flood samples of produced fluids (and hence post-flood samples of oil) are taken intermittently, the frequency of sampling may increase over time towards the point in time when it is predicted that incremental oil will breakthrough into the production well. As discussed above, initial post-flood samples of oil, taken before breakthrough of incremental oil at the production well, may be used as baseline samples of the oil. Step 210 involves analyzing the post-flood sample(s) of oil to establish post-flood compositional signatures for the oxygen-containing organic compounds in the oil.

Step 212 involves identifying a difference between one or more of the post-flood compositional signatures for the oxygen-containing organic compounds in the oil and the baseline compositional signature for the oxygen-containing organic compounds in the oil that is characteristic of incremental oil released by the low salinity waterflood. It has been found that a difference in the compositional signature for the oxygen-containing organic compounds is observed upon breakthrough of incremental oil, arising from a low salinity waterflood, into the production well 1a-1d. Thus, changes to the oxygen-containing organic compounds in the oil serve as a signature or fingerprint for the release of incremental oil during a low salinity waterflood. The method steps 210 and 212 are discussed later in more detail in relation to HRMS analytical techniques.

The difference between post-flood compositional signatures can be identified in a number of suitable ways. For example, when the baseline and post-flood compositional signatures can be expressed as a single number, the difference may be an increase, a decrease or a variance. For example the identified difference may be an increase, decrease or variance of at least 75%, at least 50%, at least 25%, or at least 10%.

The present invention allows better management of the low salinity waterflood and hence allows incremental oil recovery for the reservoir to be optimized. For example, the identification of a difference between one or more of the post-flood compositional signatures for the oxygen-containing organic compounds in the oil and the baseline compositional signature for the oxygen-containing organic compounds in the oil that is characteristic of incremental oil released by the low salinity waterflood may be used:

- as a surveillance tool for detecting movement of incremental oil through a reservoir during a low salinity waterflood;
- to confirm that incremental oil has been produced from a production well;
- to determine when to stop injecting low salinity water into an injection well and when to start injecting low salinity water into a different injection well;
- to determine the location for infill wells to optimize sweep of the reservoir by the low salinity injection water; or
- to quantify the amount of incremental oil produced by a low salinity waterflood. For example, it may be determined that the amount of incremental oil produced by a low salinity waterflood may be relatively small, and it may be determined that it is more cost effective to commence a high salinity waterflood instead.

Compositional signatures for the oxygen-containing organic compounds in the baseline and post-flood oil samples may be generated using any suitable analytical technique, in particular, High Resolution Mass Spectrometry (HRMS). In one example, a High Resolution Mass Spectrometer instrument may be part of suitably positioned measurement equipment 22, as seen in FIG. 1. This measurement equipment may be located at the production facility (for example, on a platform or FPSO) or at a remote laboratory, Data produced by the measurement equipment 22 may be analysed locally or remotely.

In HRMS, the resolution may be expressed as (m/Δm) where Δm is the width of the peak at a height which is a specified fraction of the maximum peak height. A common standard, well known to the person skilled in the art, is based on Δm being defined as the Full Width of the peak at Half its Maximum height (FWHM). The high resolution mass spectrometer used in the present invention typically has a resolution of greater than 50,000 FWHM, preferably, greater than 100,000 FWHM at a m/z value of, for example, 400. Suitable high resolution mass spectrometer instruments that may be used in the method of the present invention include Fourier Transform-Ion Cyclotron Resonance (FT-ICR) mass spectrometers, High Resolution-Time of Flight (HR-TOF) mass spectrometers, sector instruments that use a static electric sector or magnetic sector or a combination of the two as a mass analyzer, or Ion Trap (IT) mass spectrometers.

Typically, an intensity normalization of the numerical m/z data (wherein m is mass and z is charge) relative to the summed intensity of a selected class of homologous organic compounds (preferably, relative to the summed intensity of a specific DBE series within the selected class of homologous organic compounds) is then performed thereby generating a data matrix comprising normalized relative intensity data for the assigned organic ions. The class or series of homologous organic compounds used for intensity normalization may vary depending upon the type of oil that is being sampled and the ionization method used in the mass spectrometric analytical technique. Typically, the class or series of homologous organic compounds used for the intensity normalization is an abundant and stable class or series of homologous organic compounds that is naturally occurring in the oil and that does not substantially change in intensity during a low salinity waterflood, and, in particular, does not substantially change in intensity upon breakthrough of incremental oil. Optionally, one or more internal standards may be added to the crude oil samples at known concentration(s) thereby allowing a comparison of samples analyzed at different times using the same instrument, or of samples analyzed using different instruments. An example of a suitable internal standard is a fluorinated organic compound, for example, a fluorinated acid, as fluorinated organic compounds are not naturally occurring in crude oil. A fluorinated organic compound also has the advantage that fluorine has a different mass deficiency to hydrogen resulting in peaks for the ionized fluorinated organic compound being in a different m/z region of the mass spectrum than peaks for the ionized organic compounds that are components of the crude oil. The person skilled in the art will understand that addition of an internal standard(s) to the oil samples will allow intensity normalization of the numerical m/z data to be performed with greater precision. Thus, intensity normalization may be performed relative to the intensity of the internal standard(s).

Matrices of normalized numerical m/z data are thereby obtained for the baseline oil sample and for the post-flood oil samples. One or more subsets of these matrices of data may be analyzed to identify a difference in compositional signature for the oxygen-containing compounds of the post-flood oil samples relative to the baseline oil sample that is characteristic of incremental oil released by the low salinity flood. Preferably, the one or more subsets of the matrices of data are used to generate a series of plots that are compared to identify any changes in the compositional signatures for the oxygen-containing organic compounds.

Preferably, the ionization method used in the HRMS technique ionizes the oxygen-containing organic compounds to generate charged molecules (ions) and minimizes fragmentation of these ions.

Oxygen containing compounds that are found in crude oil are typically divided into:
1. Acidic compounds such as linear aliphatic carboxylic acids, branched aliphatic carboxylic acids, monocyclic naphthenic acids, bicyclic naphthenic acids, polynuclear naphthenic acids, aromatic acids, binuclear aromatic acids, polynuclear aromatic acids, phenols and cresols; and
2. Non acidic compounds such as esters, aldehydes, ketones, benzofurans and dibenzofurans.

Any suitable ionization method may be used to ionize the oxygen-containing organic compounds including: Negative Ion Electrospray Ionization, ESI(−), which is capable of ionizing oxygen-containing organic compounds such as phenols and carboxylic acids and nitrogen containing compounds such as pyrroles and pyrollidines; Positive Ion Electrospray Ionisation, ESI(+), which is capable of ionizing nitrogen-containing organic compounds such as amines and pyridines and sulphur-containing organic compounds; Negative Ion Atmospheric Pressure Photoionization, APPI (−), which is capable of ionizing aromatic hydrocarbons, phenols, pyrroles, carboxylic acids and sulfur containing hydrocarbons; and Positive Ion Atmospheric Pressure Photoionization, APPI(+), which is capable of ionizing aromatic hydrocarbons, non-acidic oxygen-containing organic compounds, phenols, cresols, pyrroles, pyridines and sulphur-containing hydrocarbons such as thiophenes. The different ionization methods used will each give a different spectrum that is characteristic of the oil sample. In one embodiment of the invention, a single ionization technique is used in the mass spectral analysis of the oil samples, preferably, this single ionization technique is ESI(−).

For ESI(−), the voltage difference at the inlet to the mass spectrometer is set so that the molecules in the sample become ionized when injected into the ionization source but do not substantially fragment. The voltage setting of a HRMS that achieves ionization while minimizing fragmentation is well known to the person skilled in the art.

For APPI, ionization is achieved via a different mechanism. Typically, the sample is irradiated with UV radiation resulting in excitation of the molecules in the oil sample with loss of electrons from the molecules resulting in the formation of radical cations. The ions may also be generated indirectly through excitation of a dopant, for example, toluene, that may be added to the oil sample.

Preferably, the oil samples are diluted with an organic solvent or a mixture of organic solvents prior to ionization. Preferred solvents for the ESI(−) ionization technique include a blend of an aromatic solvent (for example, benzene, toluene or xylene, preferably toluene or xylene) with an alcohol (for example, methanol, ethanol or 2-propanol, preferably methanol). Preferably the aromatic solvent and alcohol are blended in a ratio of from 1:1 to 3:1, in particular, about 1.5:1. Optionally, a base is added to the solvent blend to aid ionization of the oxygen-containing organic compounds. Preferred bases include ammonia or ammonium hydroxide solutions. Suitably, the concentration of ammonia in the solvent blend is in the range of 0.1 to 2% by volume (based on addition of a 35% by volume solution of ammonia in an alcohol, for example, methanol, ethanol or 2-propanol).

The diluted oil samples may be injected into the mass spectrometer using any suitable injection technique including direct infusion, or, in the case of a liquid chromatography mass spectrometer (LCMS), using flow injection analysis (FIA), by removing the liquid chromatography column and injecting the sample into a continuous flow of a carrier fluid, preferably, a liquid carrier. The liquid carrier for the LCMS spectrometer may be an organic solvent and suitable organic solvents are well known to the person skilled in the art.

Where HRMS is used as the analytical technique, the changes in the compositional signatures for the oxygen-containing organic compounds that are indicative of incremental oil released during a low salinity waterflood include one of more of the following:
1. An increase in the total normalised signal intensity of the class of homologous compounds of general formula $C_xH_yO_n$ wherein x is an integer in the range of 5 to 100 preferably 8 to 75, more preferably 8 to 60, in particular 10 to 45, y is an integer $\leq 2x+2$, and n is an integer in the range of 1 to 10, preferably, 1 to 5, more preferably, 1 to 3, in particular, 2.
2. A decrease in the intensity weighted double bond equivalent (DBE) value for the class of homologous compounds of general formula $C_xH_yO_n$ wherein x, y and n are as defined above.
3. An increase in the total normalised signal intensity of the class of homologous compounds of general formula $C_xH_yO_n$ (DBE=1) wherein x, y and n are as defined above.

The reliability of the changes to the oxygen-containing organic compounds that serve as a "signature" or "fingerprint" for the incremental oil produced during a low salinity waterflood increases with increasing specificity of the class of homologous compounds. Thus, an increase in the ratio of the total signal intensities of the class of homologous compounds of general formula $C_xH_yO_n$ (DBE=1) wherein x, y are as defined above and n=2, may be a specific marker for the incremental oil released during a low salinity flood.

The person skilled in the art will understand that DBE is a way of expressing the degree of unsaturation of an organic compound. Assignment of DBE values to each of the formulae assigned from the m/z numerical values of a mass spectrum is a long established analytical technique. A DBE of 1 corresponds to either one τ bond (C=C bond or C=O bond) or one closed fully saturated ring. It can be seen that saturated aliphatic monocarboxylic acids and saturated ketones have a DBE of 1; monocyclic naphthenic acids having a single carboxylate functional group and no sites of ethylenic unsaturation have a DBE of 2; phenol and methylphenol (cresol) have a DBE of 4; benzoic acid and phenyl acetic acid have a DBE of 5; and benzofuran has a DBE of 6. Thus, a decrease in intensity weighted DBE value for the class of homologous compounds of general formula $C_xH_yO_n$ wherein x, y and n are as defined above is indicative of a higher degree of saturation for the oxygen-containing organic compounds in the incremental oil arising from a low salinity waterflood.

Figure 3:
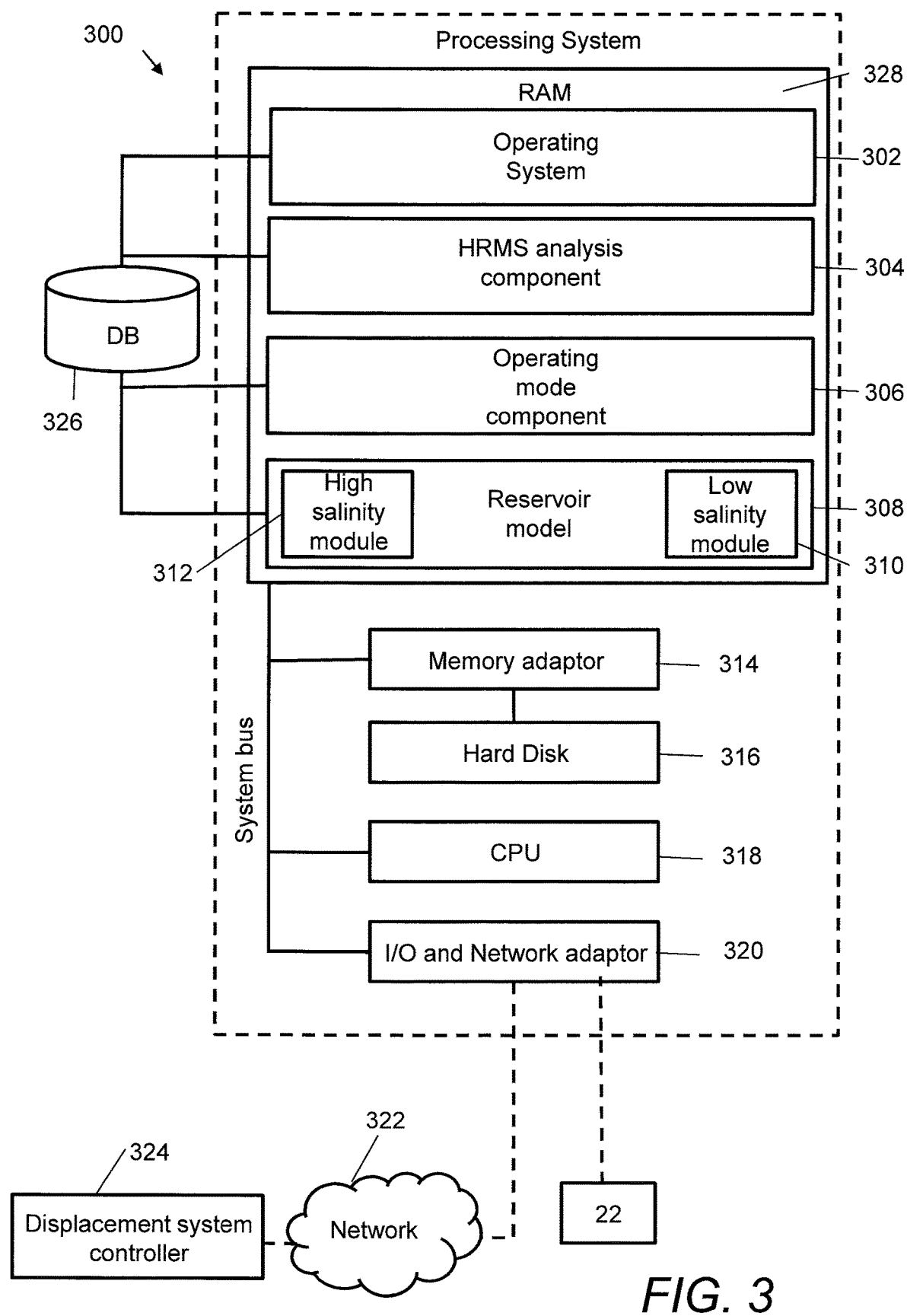
FIG. 3 is a system for carrying out any of the methods of the present invention.

System 300, shown in FIG. 3, can be used to determine when incremental oil is being recovered at a production well 1a-1d. System 300 includes a High Resolution Mass Spectrometry (HRMS) component 304 that can analyse spectra of oil samples that are obtained using a HRMS instrument. In one example, HRMS instrument may be part of suitably positioned measurement equipment 22, as seen in FIGS. 1 and 3.

In one arrangement, HRMS analysis component 304 is executed by the processing system 300, which comprises a conventional operating system and a system bus connecting a central processing unit (CPU) 318, a hard disk 316, a random access memory (RAM) 328, I/O and network adaptors 320 facilitating connection to user input/output devices and interconnection with other devices on the network 322. The RAM 328 contains operating system software 302 which controls, in a known manner, low-level operation of the processing system 300. The RAM 328 contains the HRMS analysis component 304, operating mode component 306 and the reservoir model 308 during execution thereof; each of which are configurable with measurement and/or predetermined data stored in a database (DB) 326 or other storage component which is operatively coupled or connected to the processing system 300.

Measurement data received by receiving means of the system 300 are based on measured characteristics of the oil reservoir 3 and of the aqueous displacement fluid, as explained further below. The measurement data may comprise specific measured values as directly measured by suitably positioned measurement equipment 22, such as measurement equipment comprising an HRMS instrument and, optionally, specific measured values as directly measured by a logging tool positioned within a suitably located surveillance well which can, for example, measure the water saturation of the reservoir or the salinity of the water contained in the reservoir. Alternatively measurement data may comprise ratios of values of characteristics, or may comprise values derived from a number of separate characteristic measurements, according to known techniques. Therefore, the raw measured characteristics may, if necessary or preferred, be manipulated by appropriate software, executed by the CPU 318 of the system 300, in order to generate measurement data that are suitable for inputting into the reservoir model 308, HRMS analysis component 304 or the operating mode component 306. Such manipulation may simply comprise a measurement unit conversion or the creation of a required ratio of measured values.

The system 300 may be operatively connected to a controller 324 of the crude oil displacement system, for example via the network 322. The controller 324 of the displacement system is automatically configured with the one or more operating modes determined by the system 300; the controller 324 being arranged to apply the one or more operating modes.

The method 200, as shown in FIG. 2, may be completely, or partially performed by the system 300. Measurement data relating to the baseline and post-flood samples of oil may be received from measurement equipment 22 which is connected to the network adaptor 320. For example, HRMS data may be received by the system 300 and stored on the hard disk 316. The HRMS analysis component 304 comprises software executed by the CPU 318 to analyse data from the HRMS instrument to determine a compositional signature of the oil sample. The HRMS analysis component 304 therefore analyses and/or manipulates data associated with the baseline sample(s) of oil and post-flood sample(s) of oil. The data may be optionally displayed on a computer monitor or stored for later use.

The HRMS analysis component 304 may also be programmed to identify a difference between the one or more of the post-flood compositional signatures for the oxygen-containing organic compounds in the oil and the baseline compositional signature for the oxygen-containing organic compounds in the oil that is characteristic of incremental oil released by the low salinity waterflood. Alternatively, such an identification can be performed manually.

In a tertiary low salinity waterflood, the changes to the compositional signatures for the oxygen-containing organic compounds typically occur in a bank of oil that breaks through into a production well 1a-1d. Accordingly, the changes to the compositional signature for the oxygen-containing organic compounds in the oil may be used as a surveillance tool during a low salinity water flood to determine when a bank of oil reaches a production well 1a-1d. Typically, the arrival of the bank of oil at a production well corresponds to an increase in the oil to water ratio in the fluids produced from the well.

The person skilled in the art would understand that when a low salinity waterflood is performed in tertiary recovery mode following a conventional waterflood with a high salinity water, the moveable oil may have already been substantially swept from the reservoir such that low salinity water serves to release adhering oil from the surface of the reservoir rock and to sweep the resulting bank of incremental oil towards the production well. In contrast, when a low salinity waterflood is performed in secondary recovery mode, the function of the low salinity water is to sweep moveable oil (i.e. oil that would be produced using a conventional high salinity waterflood) ahead of the low salinity water towards the production well and to release adhering incremental oil from the surface of the reservoir rock. Without wishing to be bound by any theory, a bank of incremental oil will therefore form between the front of the low salinity waterflood and the tail of the moveable oil thereby extending the period of "dry" oil production before breakthrough of injected water into the production well (in comparison with the period of "dry" oil production for a conventional high salinity flood). There may be dispersive mixing between the bank of incremental oil and the moveable oil. Accordingly, the difference in the compositional signature for the oxygen containing organic compounds upon breakthrough of incremental oil at the production well may be less marked in secondary recovery mode than for tertiary recovery mode. More frequent sampling and analysis of the produced oil may therefore be required for a secondary low salinity waterflood than for a tertiary low salinity waterflood.

The person skilled in the art will also understand that the amount of incremental oil that may be potentially produced from an oil reservoir during a low salinity waterflood may be determined by: (1) taking a core plug from a sample of the reservoir rock and performing a coreflood experiment using a baseline secondary high salinity waterflood, such as a seawater flood, followed by a tertiary low salinity waterflood, or (2) taking two "sister" core plugs from a sample of the reservoir rock and performing a secondary low salinity waterflood on the first core plug and a secondary baseline high salinity waterflood on the second core plug. By "sister plugs" is meant rock samples taken from part of a core having similar rock properties. These coreflood experiments may be performed under either reservoir conditions or reduced conditions. A reduced condition coreflood test employs dead fluids (crude oil and waters that do not contain any gas) while a reservoir condition coreflood test employs live fluids (crude oil and waters that have been combined with a gas having the same or similar composition to the gas that was separated from the produced fluids at a production facility). In both cases, the crude oil is preferably sampled from the same reservoir from which the sample of reservoir rock is taken. Changes to the compositional signature for the oxygen-containing organic compounds in the oil produced during the low salinity coreflood experiment relative to the oil produced during the baseline high salinity coreflood experiment may then be correlated with production of incremental oil during the low salinity coreflood test. In particular, the normalized relative signal intensity of one or more of the above defined classes of homologous oxygen-containing organic compounds characteristic of the incremental oil released by the low salinity coreflood may be used for this correlation. The coreflood experiment may therefore be used to determine the compositional signature for the oxygen-containing organic compounds that is the most abundant and/or most specific marker for the incremental oil that may be potentially produced from the reservoir during a low salinity waterflood.

In one aspect of the present invention, the change in the compositional signature for the oxygen-containing organic compounds in the oil relative to the baseline oil sample may be used to history match a reservoir simulation of a low salinity waterflood to measurement data obtained during a low salinity waterflood of a reservoir. History matching a reservoir simulator is well known to those skilled in the art. History matching involves adjusting a simulation of a reservoir until it closely reproduces the past behaviour of a reservoir. A history matched model can therefore be used to simulate future reservoir behaviour with a higher degree of confidence.

Commercial reservoir simulators that model low and high salinity waterfloods are available. One such commercial simulator is Eclipse, commercially available from Schlumberger. Furthermore, the technical paper "Modeling Low-Salinity Waterflooding (SPE 102239)" by G. R. Jerauld et al. describes how to adapt a reservoir simulator to model low salinity waterflooding. Current reservoir models, such as Eclipse, can model both low and high salinity waterfloods. For example, a modelled high salinity waterflood may predict that the total volume of oil produced is $V_{high\ salinity}$. Keeping all other inputs the same, and instead modelling a low salinity waterflood, the model may predict the total volume of oil produced is $V_{low\ salinity}$. The amount of incremental oil that is produced due to the low salinity waterflood is therefore given by $V_{incremental}=V_{low\ salinity}-V_{high\ salinity}$, where $V_{low\ salinity}>V_{high\ salinity}$.

Although these conventional reservoir simulators are able to model low and high salinity waterfloods to determine, amongst other things, the amount of oil that would be produced during such a waterflood, the modelled output(s) may be inaccurate. For example, modelled output(s) may not match what occurs during a real waterflood of a particular reservoir. One source of error during a simulation could be due to uncertainty in the data input into the models. Uncertainty of the input(s) into the model can therefore have an effect on the modelled output(s). History matching involves varying the input(s) into the model and comparing the modelled output(s) to what is observed/measured during a real waterflood. The step of varying of the input(s) may be performed iteratively, until there is good agreement between the modelled output(s) and the measured output(s). For example, the difference between the modelled output(s) and the measured output(s) may be minimised until the difference is less than an acceptable threshold, for example a variance of less than 10%, more preferably less than 5%, more preferably less than 1% between the modelled output and the measured outputs. In other examples, absolute thresholds may also be used, for example a define absolute value of the tolerance.

Once a history matched model has been produced, the volume of incremental oil produced in future low salinity waterfloods may be calculated. This involves comparing the modelled volume of oil produced during a high salinity waterflood to the modelled volume of oil produced during a low salinity waterflood. The predicted amount of incremental oil is likely to more closely match what would be observed because the models have been history matched. Decisions whether to perform low salinity waterfloods can therefore be made depending on the predicted volume of incremental oil. For example, it may be more cost effective to perform a high salinity waterflood than to desalinate sea water if the predicted volume of incremental oil is low.

One possible observed/measured output that can be used for history matching, is the time at which incremental oil breaks through into a production well 1a-1d. Alternatively or additionally, the measured volume of oil produced as a function of time can be used to history match the model. This measured time at which incremental oil breaks through into a production well can be determined using the method 200 of FIG. 2. As explained above, the method 200 can detect the presence of incremental oil in the produced oil. This may then be used to determine the time at which incremental oil is observed in the production well 1a-1d after commencing the low salinity waterflood. Once the time at which incremental oil breaks through into the production well of the reservoir has been measured, this value can be used to history match the reservoir model.

As was briefly explained above, a reservoir simulator may be used to assess the amount of incremental oil that may be potentially produced during a low salinity waterflood at the reservoir scale. A reservoir simulator is well known to the person skilled in the art and is used to model or simulate injection of fluids into one or more layers of a reservoir via injection well(s), movement of fluids through the layer(s) of the reservoir, and production of fluids from the layer(s) of the reservoir via production well(s). Typically, a static geological model of the reservoir is imported into the reservoir simulator. This static geological model is obtained by inputting seismic imaging data, petrophysical data associated with the layer(s) of reservoir rock (for example, the porosity and absolute permeability of the layer(s) of reservoir rock) and a geological description of the layer(s) of reservoir rock (for example, mineralogical characteristics of the layer(s) of reservoir rock) and fluid saturation data (for example, the initial water saturation and initial oil saturation of the reservoir) into a geological model thereby generating a 3 dimensional (3-D) model of the reservoir showing the layer(s) of the reservoir rock, traps, any faults or any regions of low permeability.

After importing the static geological model into the reservoir simulator, the locations of the injection well(s) and production well(s) are selected and inputted into the reservoir simulator. Additional fluid data is also inputted into the reservoir simulator such as the connate water characteristics (for example, the total dissolved solids (TDS) content of the connate water and the content of one or more of the individual dissolved ions), oil characteristics (for example, the chemical composition, density and viscosity of the oil), characteristics of a low salinity injection water (for example, the TDS content of the low salinity water and the content of one or more of the individual dissolved ions) and characteristics of a baseline high salinity injection water (for example, the TDS content of the high salinity water and the content of one or more of the individual dissolved ions). The relative permeabilities of the reservoir rock to oil and water measured at the salinities of the low salinity injection water and the baseline high salinity injection water are also inputted into the reservoir simulator. In the event that the rock properties (porosity, absolute permeability or mineralogical characteristics) vary across the reservoir (for example, the rock characteristics vary between layer(s) of reservoir rock or spatially across the reservoir), the measured relative permeabilities to oil and water for the different rock types are inputted into the reservoir simulator. As is well known to the person skilled in the art, the relative permeabilities of the reservoir rock to oil and water may be determined from coreflood experiments performed on samples of reservoir rock under reservoir conditions. Typically, the relative permeabilities of the reservoir rock to oil and water are measured as a function of increasing water saturation (decreasing oil saturation) thereby generating relative permeability curves. As is explained in "Modeling Low-Salinity Waterflooding (SPE 102239)" by G. R. Jerauld et al., relative permeability and capillary pressure are a function of salinity. High and low salinity relative permeability curves are inputs into the reservoir model, and may be interpolated for salinities in between.

The data relating to the characteristics of the low salinity water and to the relative permeabilities of the reservoir rock to oil and water measured at the salinity of the low salinity water are hereinafter referred to as "low salinity input data". The data relating to the characteristics of the baseline high salinity water and to the relative permeabilities of the reservoir rock to oil and water measured at the salinity of the baseline high salinity water are hereinafter referred to as "high salinity input data". The remaining data inputted into the reservoir simulator are hereinafter referred to as "common input data". For example, common input data can comprise locations of the injection well(s) and production well(s) and fluid data comprising characteristics of the connate water and oil associated with the layer(s) of the reservoir rock.

The reservoir simulator then uses the common input data and the low salinity input data to model, as a function of time, injection of low salinity water into the reservoir via the injection well(s), movement of fluids through one or more layers of the reservoir, in particular, the oil-bearing layer(s), and production of fluids from the reservoir via the production well(s), taking into account barriers to flow in the geological model such as faults or a reduction in permeability of the reservoir rock. The resulting reservoir simulation thereby provides various low salinity output data including:

(a) the volumetric sweep efficiency for the one or more layers of the reservoir;

(b) the time at which low salinity water will break through into the production well(s);

(c) pressures in the injection well(s) and production well(s), in particular, the pressures in the injection well(s) and production well(s) at the depth(s) of the oil-bearing layer(s) of the reservoir; and (d) the volumes of oil and water produced from the production well(s) during a low salinity waterflood of the reservoir, as a function of time (thereby providing a "low salinity" oil production profile).

In some examples, the time at which incremental oil breaks through into the production well(s) can also be modelled, or inferred from the low salinity output data.

The person skilled in the art will understand that one or more of low salinity output data (a) to (c), preferably, all of the low salinity input data (a) to (c) may be used as additional input data for the reservoir simulator when calculating the volume(s) of oil and water that would be produced from the production well(s) during a low salinity waterflood, as a function of time. Volumetric sweep efficiency provides an indication of the fraction of the reservoir which has been swept or not swept by the injected water.

The reservoir simulation may then be re-run using the common input data and the high salinity input data to provide high salinity output data including:

(a) the volumetric sweep efficiency for the one or more layers of the reservoir;

(b) the time at which high salinity water will break through into the production well(s);

(c) pressures in the injection well(s) and production well(s), in particular, the pressures in the injection well(s) and production well(s) at the depth(s) of the oil-bearing layer(s) of the reservoir; and (d) the volumes of oil and water that would be produced from the production well(s) during a high salinity waterflood, as a function of time (thereby providing a "high salinity production profile).

The person skilled in the art will understand that one or more of the high salinity output data (a) to (c), preferably, all of high salinity output data (a) to (c) may be used as additional input data for the reservoir simulator when calculating the volumes of oil and water that would be produced from the production well(s) during a high salinity waterflood, as a function of time.

The person skilled in the art will understand that, at any point in time, the difference in the volume of oil produced from the production well(s) between the simulated high salinity waterflood and the simulated low salinity waterflood, is an estimate for the volume of incremental oil that may be potentially obtained during a low salinity waterflood of the reservoir.

History matching is then performed by inputting reservoir measurement data into the reservoir model. This reservoir measurement data includes the time at which incremental oil was found to breakthrough into the production well(s) (as determined by detecting a change in post-flood composition signature for the oxygen containing compounds in the oil compared with the baseline compositional signature for the oil). Preferably, the reservoir measurement data also includes one or more of:

a) The volume of low salinity water injected into the injection well(s) as a function of time, for example, the volume of low salinity water injected into each injection well per day;

b) The volume of oil produced from the production well(s) as a function of time, for example, the volume of oil produced from each injection well per day;

c) The volume of water produced from the production well(s) as a function of time, for example, the volume of water produced from each production well per day;

d) The water-cut for the reservoir as a function of time (wherein "water-cut" is the ratio of the volume of water to the volume of oil produced from the reservoir), in particular, the water-cut for each production well as a function of time;

e) The downhole pressures in the injection well(s) and production well(s) at the depth(s) of the oil bearing layer(s) of the reservoir as a function of time;

f) The salinity of the produced water as a function of time;

g) The concentrations of selected ions in the produced water as a function of time, for example, the concentrations of divalent cations such as magnesium or calcium cations as a function of time;

h) The time at which low salinity water was found to breakthrough into the production well(s);

i) In the event that a surveillance well penetrates the reservoir (as discussed below), the water saturation of the oil-bearing layer(s) of reservoir rock surrounding the surveillance well as a function of time and/or the salinity of the water contained in the pore space of the oil-bearing layer(s) of reservoir rock surrounding the surveillance well as a function of time;

j) If available, four-dimensional (4-D) seismic imaging data i.e. seismic imaging data obtained at one or more points in time following commencement of oil production from the reservoir.

History matching of the reservoir simulation output data (including the predicted oil production volumes for the low salinity waterflood simulation) to the reservoir measurement data is then performed by adjusting uncertainties in the input data (for example, uncertainties in the static geological model, uncertainties in the petrophysical data or, uncertainties in the relative permeability data). These adjustments are continued until a match is obtained between the reservoir simulator output data and the reservoir measurement data. The person skilled in the art will understand that as the low salinity waterflood proceeds, the history matching step may be repeated, one or more times, such that the output data of the reservoir simulation continues to closely match the reservoir measurement data. The history matching of the low salinity waterflood may be performed by adjusting uncertainties in only the low salinity input data, only the common input data or in both the common input data and the low salinity input data. When the uncertainty in the common input data is adjusted, the history matched common input data can also be used in a high salinity reservoir simulation.

The validated (history matched) reservoir simulator may then be used in predictive mode to estimate future incremental oil production from the reservoir arising from the low salinity waterflood or to provide strategies for improved management of the low salinity waterflood in the reservoir, for example, by modelling changes in the amounts of low salinity water injected into one or more of the injection wells or by ceasing injection of low salinity water into one or more of the injection wells and commencing injection of low salinity water into one or more different injection wells.

In yet a further aspect of the present invention, the change in compositional signature for the oxygen-containing compounds in the oil relative to the baseline oil sample may be used to provide an estimate for the amount of incremental oil produced from the reservoir. As discussed above, a history match of the reservoir simulation is performed following incremental oil breakthrough into the production well(s) of the reservoir such that the predicted volumes of produced oil and water for the low salinity waterflood match the actual volumes of oil and water produced from the reservoir. History matching of the reservoir simulation is performed on a regular basis as the low salinity waterflood proceeds such that the predicted volumes of produced oil and water obtained using the reservoir simulator continue to closely match the actual volumes of oil and water produced from the reservoir. After history matching the reservoir simulation output data to the reservoir measurement data, an estimate for the incremental oil production achieved as a result of the low salinity waterflood may be obtained by running the history matched reservoir simulator using the high salinity input data. For example, the history matched reservoir simulator uses the history matched common input data or any other history matched input data. The history matched reservoir simulator therefore provides predicted volumes of produced oil and water that would have been achieved if the reservoir was flooded with the baseline high salinity injection water and not the low salinity injection water. The difference in the actual volume(s) of oil produced from the production well(s) of the reservoir and the predicted volumes obtained using the history matched high salinity reservoir simulation provides an estimate for the volume of incremental oil arising from the low salinity waterflood. As discussed above, history matching of the low salinity reservoir simulation is carried out on a regular basis during the low salinity waterflood of the reservoir. Accordingly, each history matched reservoir simulation may be run using the high salinity input data, thereby providing estimates for the incremental oil production as the low salinity waterflood progresses.

The person skilled in the art will understand that when the history matched reservoir simulation is run using the high salinity input data, estimates may also be provided for the extended period of dry oil recovery achieved as a result of a secondary low salinity waterflood or the extended period of reduced water-cut achieved as a result of a tertiary low salinity waterflood. Thus, the measured time(s) at which low salinity water breaks through into the production well(s) during a secondary low salinity waterflood or the measured water-cut(s) for the fluids produced from the production well(s) during a tertiary low salinity waterflood may be compared with the modelled water breakthrough time(s) or the modelled water-cut(s) obtained when the history matched reservoir simulation is run using the high salinity input data.

System 300, as shown in FIG. 3, can be used to history match a reservoir simulation to measurement data. System 300 includes a reservoir model 308 that can simulate a waterflood. Reservoir model 308 includes a low salinity module 310 and a high salinity module 312. When the reservoir model 308 uses the low salinity module 310, it can be used to model a low salinity waterflood. When the reservoir model 308 uses the high salinity module 312, it can be used to model a high salinity waterflood. The CPU 318 may cause the reservoir model 308 to model a plurality of waterfloods simultaneously or individually. Reservoir measurement data, used in history matching the reservoir simulation output data, can be obtained by the reservoir model 308 from the HRMS analysis component 304. For example, this reservoir measurement data can comprise the time at which incremental oil was found to breakthrough into the production well(s) (as determined by detecting a change in post-flood composition signature for the oxygen containing compounds in the oil compared with the baseline compositional signature for the oil). Additional reservoir measurement data, listed above, may be obtained by the reservoir model 308 from one or more of the database 326, hard disk 316 or measurement equipment 22. The reservoir model 308 can then perform history matching to more accurately predict the amount incremental oil produced during a low salinity waterflood.

Based on the modelled output(s) of the history matched reservoir simulations, operating mode component 306 may, for example, determine when to stop injecting low salinity water into an injection well and when to start injecting low salinity water into a different injection well. Operating mode component 306 obtains the results from the analysis performed by the reservoir model and can select several operating modes of the displacement system accordingly. Displacement system controller 324 of the crude oil displacement system is connected to the system 300. The controller 324 applies one or more operating modes determined by the operating mode component 306. In another example, operating mode component 306 may determine which injection well 10 to inject low salinity water into based on the output received from the reservoir model 308. For example, the reservoir model may predict that injection into one injection well will produce more incremental oil than if water was injected into another injection well.

Figure 4:
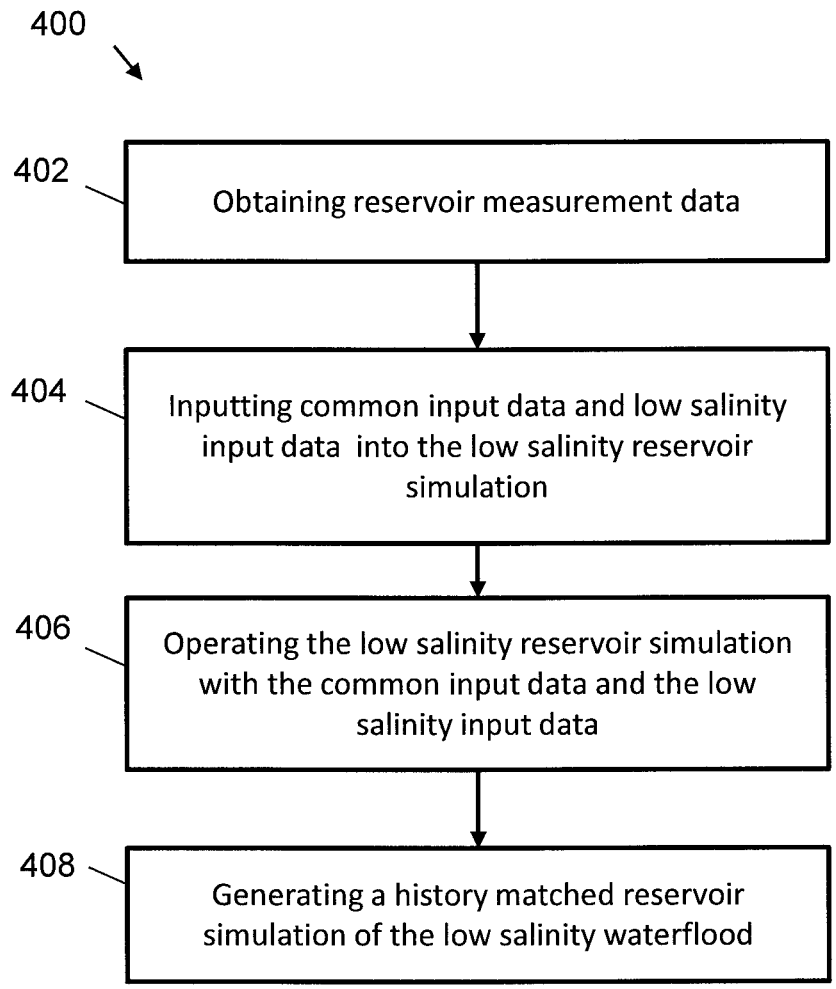
FIG. 4 is a flow diagram showing a method of history matching a low salinity reservoir simulation to reservoir measurement data.

FIG. 4 is a flow diagram showing a method 400 of history matching a low salinity reservoir simulation to reservoir measurement data. In one example, the method 400 is performed using the reservoir model 308 of FIG. 3. The method 400 comprises, at step 402, obtaining reservoir measurement data. For example, the production time(s) at which incremental oil breaks through into the production well(s) during a low salinity waterflood may be determined, using the method 200 of FIG. 2 described above. Additional reservoir measurement data that may be obtained includes the measured volume(s) of oil produced from the production well(s) during the low salinity waterflood, as a function of time.

In step 404, the method comprises inputting common input data and low salinity input data into the low salinity reservoir simulation to simulate the low salinity waterflood, wherein the common input data and the low salinity input data have associated uncertainties. Step 406 comprises operating the low salinity reservoir simulation with the common input data and the low salinity input data to generate low salinity output data, the low salinity output data comprising one or more of:

the calculated volumetric sweep efficiency for the layer(s) of the reservoir rock, as a function of time;

the calculated time(s) at which the low salinity water breaks through into the production well(s);

the calculated pressures in the injection well(s) and production well(s) at the depth of the oil-bearing layer(s) of the reservoir; and the calculated volume(s) of oil produced from the production well(s), under low salinity conditions, as a function of time.

In step 408, the method comprises generating a history matched reservoir simulator of the low salinity waterflood by history matching the low salinity output data to the reservoir measurement data by adjusting the uncertainties in the low salinity input data. In some examples, generating a history matched reservoir simulator comprises adjusting the uncertainties in the common input data to generate history matched common input data.

The method may also optionally comprise importing a static three-dimensional (3-D) geological model of the reservoir into the reservoir simulator showing the layer(s) of the reservoir rock and any barrier(s) to flow and incorporating petrophysical data, rock characteristic data, and fluid saturation data, for the layer(s) of the reservoir rock. In some examples, this input data can also be adjusted during history matching.

Optionally, the volume of incremental oil produced from the reservoir can be estimated, as a function of time, using the history matched reservoir simulation generated according to method 400. A method of estimating the volume of incremental oil, as a function of time, comprises:

inputting high salinity input data into the history matched reservoir simulator to simulate a high salinity waterflood;

operating the history matched reservoir simulator using the history matched common input data and the high salinity input data to generate high salinity output data, the high salinity output data including the calculated volume(s) of oil produced from the production well(s), under high salinity conditions, as a function of time; and estimating the volume of incremental oil by subtracting the calculated volume(s) of oil produced from the production well(s), as a function of time under high salinity conditions from the measured volume(s) of oil produced from production well(s) during the low salinity waterflood of the reservoir, as a function of time. Those skilled in the art will appreciate that any, or all, history matched input data can be used in the history matched simulator.

Figure 5:
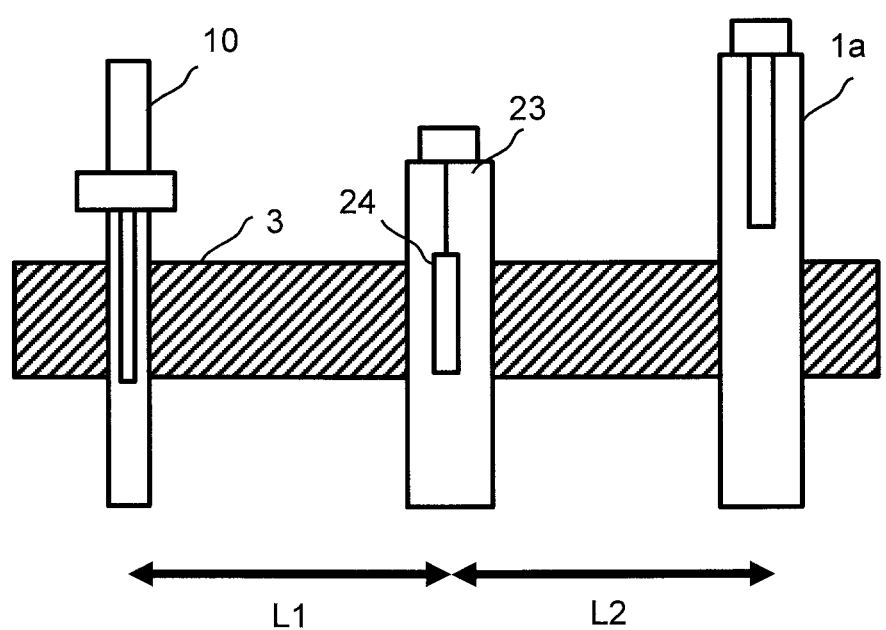
FIG. 5 is a schematic diagram showing a surveillance well located between an injection well and a production well.

As mentioned above, the reservoir may be optionally penetrated by a surveillance well into which may be lowered a logging tool. For example, the logging tool may be operable to measure the water saturations of the oil-bearing layer(s) of reservoir rock or the salinity (total dissolved solids content) of the water contained in the pore space of the oil-bearing layer(s) of reservoir rock may be arranged in the surveillance well. FIG. 5 shows such a surveillance well 23 penetrating the reservoir 3. In this example, the surveillance well 23 penetrates the reservoir 3 between the injection well 10 and the production well 1a. The surveillance well 23 also comprises a logging tool 24 which can, for example, measure the water saturation or salinity of the water contained in the reservoir 3.

Changes in the water saturations (and hence changes in the oil saturations) of one or more of the oil-bearing layers of reservoir rock can be correlated with production of incremental oil from the production well. The person skilled in the art will understand that a change in water saturation of the oil-bearing layer(s) of reservoir rock is indicative of a change in oil saturation wherein percentage oil saturation is [100−water saturation %]. Thus, for a tertiary low salinity waterflood, when a bank of oil is swept through the region of the reservoir penetrated by the surveillance well, there will be changes to the water saturation of the oil-bearing layer(s) of reservoir rock. In particular, as the bank of oil reaches the surveillance well, there will be an increase in oil saturation and a decrease in water saturation of the reservoir rock (in comparison with a baseline oil saturation and water saturation of the reservoir rock at commencement of the low salinity waterflood). As the tail of the bank of oil moves past the surveillance well, there will be a decrease in oil saturation and an increase in water saturation of the reservoir rock (in comparison with a baseline oil saturation and water saturation of the reservoir rock at commencement of the tertiary low salinity waterflood). The person skilled in the art will understand that after the tail of the bank of oil has moved past the surveillance well, the reservoir rock will be at residual oil saturation, $S_{or}$.

For a secondary low salinity waterflood, there will be a decrease in oil saturation and an increase in water saturation of the reservoir rock as the tail of the bank of oil moves past the surveillance well (in comparison with a baseline oil saturation and water saturation of the reservoir rock at commencement of the secondary low salinity waterflood). The person skilled in the art will understand that after the tail of the bank of oil has moved past the surveillance well, the reservoir rock will be at residual oil saturation, $S_{or}$.

Changes in the salinity of the water contained in the pore space of the oil-bearing layer(s) of reservoir rock may be used to monitor the rate of advancement of the front of the low salinity waterflood in the one or more oil-bearing layer(s) of the reservoir. Thus, there will be a decrease in the salinity of the water contained in the pore space of the oil-bearing layer(s) of reservoir rock as the front of the low salinity waterflood moves past the surveillance well. The data associated with detection of low salinity water at the production well may therefore be used to history match the reservoir simulator to provide greater certainty for the prediction of when low salinity water will break through into the production well(s). This data may also be used to determine when to increase the frequency at which post-flood samples of oil are taken for analysis of the oxygen-containing organic compounds in the produced oil.

The paper "Modeling Low-Salinity Waterflooding (SPE 102239)" by G. R. Jerauld et al. shows how the oil and water saturation and salinity changes as a function of distance from the injection well during secondary and tertiary low salinity waterfloods. Jerauld et al. show "shocks" in the saturation as a function of distance from the injection well at a particular moment in time. These shocks relate to regions where the salinity and saturations abruptly varies as oil and water are swept through the reservoir rock. A person skilled in the art will appreciate that by monitoring the salinity or saturation over time, the front of the low salinity water can be detected as it moves past the surveillance well. For example, by plotting the salinity or saturation over time "shocks" as described in. Jerauld et al may be identified.

In another example, differences in baseline and post-flood salinity and saturation measurements can be detected. A difference between one or more post-flood measurements can be detected that is characteristic of the front of the low salinity waterflood. For example, the difference may be an increase, a decrease or a variance. For example the identified difference may be an increase, decrease or variance of at least 50%, at least 75%, or at least 90%. Typically, the baseline salinity of the water contained in the pore space of the reservoir rock may be in the range of 15,000 to 350,000 ppmv. The post-flood salinity of the water contained in the pore space of the reservoir rock, after the front of the low salinity water has moved past the surveillance well, may be in the range of 200 to 12,000 ppmv, preferably 500 to 10,000 ppmv, more preferably, 500 to 5,000 ppmv.

In another example, the front of the low salinity water can be detected at a surveillance well by detecting the presence of a tracer that has been introduced into the low salinity water. This tracer could be used to predict when the front of the low salinity waterflood reaches a production well.

Figure 6:
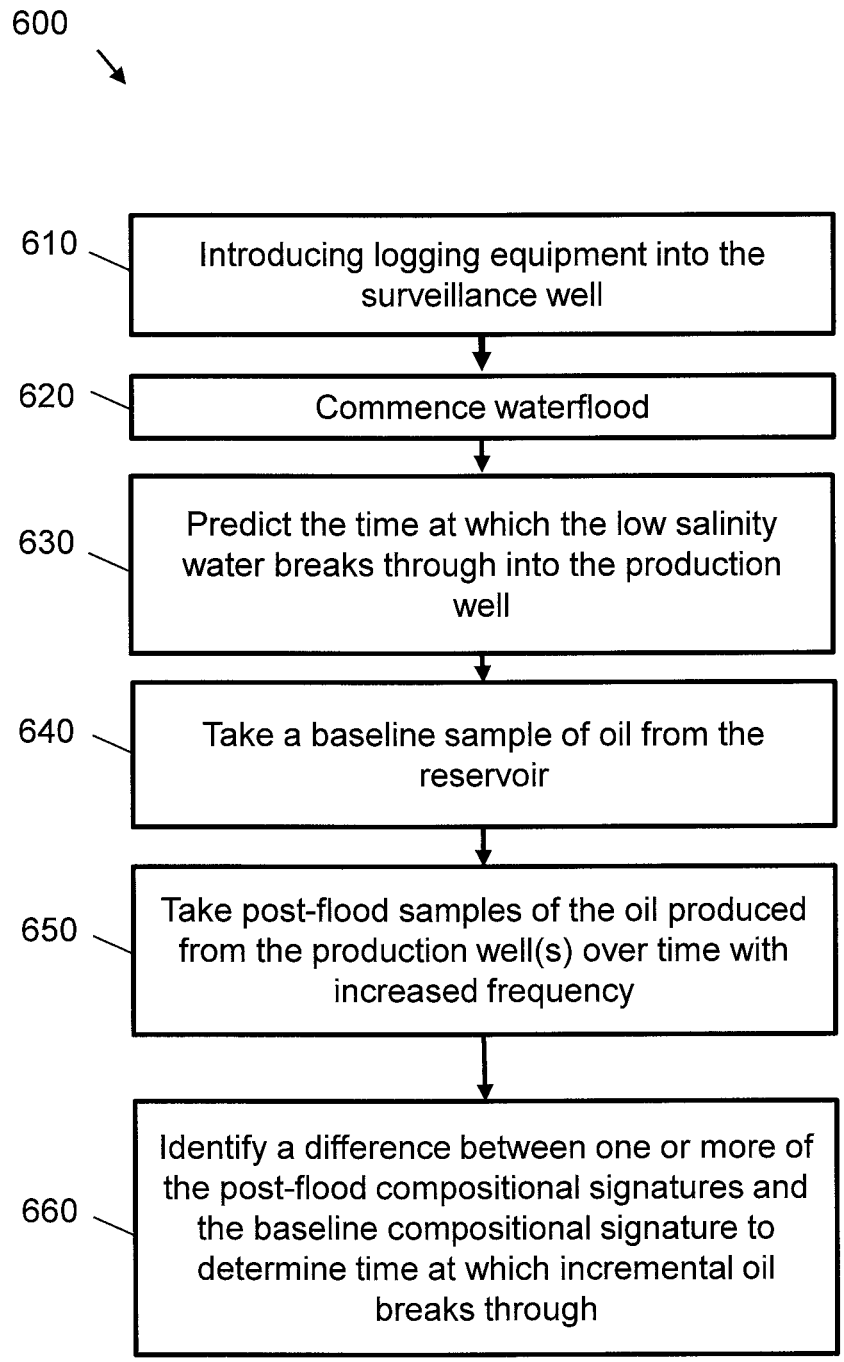
FIG. 6 is a flow diagram showing a method for detecting incremental oil production from an oil-bearing reservoir comprised of a plurality of layers of reservoir rock wherein the reservoir is penetrated by at least one injection well, at least one production well and at least one surveillance well located between the injection well and production well.

In FIG. 6, there is provided a method 600 for detecting incremental oil production from an oil-bearing reservoir 3 comprised of a plurality of layers of reservoir rock wherein the reservoir 3 is penetrated by at least one injection well 10, at least one production well 1a and at least one surveillance well 23 located between the injection well 10 and production well 1a, the method comprising, in step 610, introducing logging equipment 24 into the surveillance well 23. In one example, the logging equipment can detect the presence of a tracer in the water. In another example, the logging equipment 24 is operable to monitor changes in the water saturation of one or more layers of reservoir rock 3, changes in the salinity of the water contained within the pore space of the layer(s) of reservoir rock 3, or changes in both the water saturation and salinity of the water. The method 600 may be completely or partially carried out by system 300.

In one example, the method optionally comprises utilizing the logging equipment 24 to establish baseline readings. For example baseline readings may be established for the water saturation of one or more of oil-bearing layers of reservoir rock 3, baseline readings for the salinity of the water contained in the pore space of one or more of the oil-bearing layers of the reservoir rock 3, or baseline readings for both the water saturation and salinity of the water. If the presence of a tracer is being detected to detect the front of the low salinity waterflood, a baseline measurement may not be required.

In step 620, the method comprises commencing the waterflood by injecting a low salinity water into the reservoir 3 from the injection well 10 and recovering oil from the production well 1a. In one example, a tracer is optionally introduced into the low salinity water. The salinity of the low salinity water may already be known.

In step 630, the method comprises utilizing the logging equipment over time. For example, post-flood readings may be taken over time for the water saturation of the oil-bearing layer(s) of reservoir rock, for the salinity of the water contained in the pore space of the oil-bearing layer(s) of reservoir rock, or for both the water saturation and salinity of the water. In one example, post-flood readings are taken to detect the presence of the tracer.

Step 630 further comprises determining the period of time, $t_1$, between commencing injection of low salinity water into the reservoir from the injection well(s) and the detection of the front of the low salinity water at the surveillance well. For example, this may comprise identifying a difference between one or more of the post-flood readings and the baseline readings for the water saturation of the oil-bearing layer(s) of reservoir rock, the salinity of the water contained in the pore space of the oil-bearing layer(s) of reservoir rock, or both the water saturation and salinity of the water, such that the difference is operable to identify a change in water saturation in the oil-bearing layer(s) of reservoir rock, a change in salinity of the water contained in the pore space of the oil-bearing layer(s) of reservoir rock, or a change in both the water saturation and salinity of the water in the vicinity of the surveillance well characteristic of the front of the low salinity waterflood reaching the surveillance well. In another example, the presence of the tracer is detected that is characteristic of the front of the low salinity waterflood reaching the surveillance well.

Step 630 further comprises, determining the interwell distance, $L_1$, between the injection well(s) and surveillance well, and calculating the velocity, v, at which the front of the low salinity water advances through the reservoir wherein $v=L_1/t_1$. Step 630 also comprises determining the interwell distance, $L_2$, between the surveillance well and production well(s) and using the frontal advance velocity, v, to predict the time, $t_2$, at which the low salinity water breaks through into the production well wherein $t_2=t_1+L_2/v$. Distances $L_1$ and $L_2$ are depicted in FIG. 5.

In step 640, the method comprises taking a baseline sample of oil from the reservoir and analyzing the baseline sample of oil to establish a baseline compositional signature for the oxygen-containing organic compounds in the oil.

In step 650, the method comprises taking post-flood samples of the oil produced from the production well(s) over time and analyzing the samples of oil to establish post-flood compositional signatures for the oxygen-containing organic compounds in the oil to identify a difference between one or more of the post-flood compositional signatures for the oxygen-containing organic compounds in the oil and the baseline compositional signature for the oxygen-containing organic compounds in the oil that is characteristic of incremental oil released by the low salinity waterflood.

Step 650 is repeated with increasing the frequency or reduced time between measurements as the time approaches the predicted time, $t_2$, at which low salinity injection water breaks through into the production well.

In step 660, the method comprises using the identified difference between the post-flood and baseline composition signatures for the oxygen-containing organic compounds in the oil to determine the time at which incremental oil breaks through into the production well.

Any residual oil saturation data obtained for the oil-bearing layer(s) of the reservoir rock by measuring the water saturation of the layers of reservoir rock after the tail of the bank of oil (in tertiary recovery mode) or the tail of the bank of incremental oil (in secondary recovery mode) has passed the surveillance well may also be inputted into a reservoir simulator such as reservoir model 308 for use in history matching the reservoir simulation to the volumes or produced oil and water. For example, the logging equipment may form part of measurement equipment 22 as shown in FIG. 3.

Baseline and post-flood samples of oil are as defined above.

Where there is more than one injection well 10 and more than one production well 1a-1d, it is preferred that a surveillance well 23 is provided for each pair of injection and production wells.

The logging equipment 24 may include a resistivity logging tool, an NMR logging tool or any other logging tool having the capability to identify changes in water saturation of the oil-bearing layer(s) of reservoir rock or changes in salinity of the water contained in the pore space of the oil-bearing layers of reservoir rock. Where the logging equipment 24 includes a resistivity logging tool or a nuclear magnetic resonance (NMR) tool, the surveillance well is preferably provided with a fibre glass casing to prevent ingress of reservoir fluids into the surveillance well.

Preferably, the surveillance well 23 is arranged substantially parallel to the production well 1a-1d. Preferably, the surveillance well 23 is located close to the production well 1a-1d such that changes in the water saturation of the layers of reservoir rock 3 at the surveillance well 23 are a good match for changes in water saturation of the layers of reservoir rock 3 at the production well 1a-1d. Preferably, the surveillance well 23 is within 30.5 m (100 feet), more preferably, within 15.2 m (50 feet) of the production well 1a-1d, in particular, within 7.6 m (25 feet) of the production well 1a-1d. Suitably, the surveillance well 23 is located 3.0 to 30.5 m (10 to 100 feet), preferably, 4.6 to 15.2 m (15 to 50 feet), in particular, 4.6 to 7.6 m (15 to 25 feet) from the production well 1a-1d.

The post-flood samples of oil may be taken either continuously or intermittently, as described above. Suitably, the baseline sample of oil and post-flood samples of oil may be analyzed for a compositional signature for the oxygen-containing organic compounds in the oil using HRMS, as described above.

The person skilled in the art will understand that water is typically co-produced with the oil from the production well(s) 1a-1d. Accordingly, the fluids produced from the reservoir are typically separated into an oil phase, water phase and gas phase at a production facility and samples of the separated oil are then analyzed for the oxygen-containing organic compounds, as described above. Optionally, the produced water may also be sampled over time and analyzed for an increase in the concentration of one or more ions, for example, $Fe^{2+}$, $Ca^{2+}$, $Mg^{2+}$ and $Sr^{2+}$ ions, in particular, $Ca^{2+}$ and $Mg^{2+}$ ions, associated with breakthrough of a low salinity water into the production well(s) 1a-1d. The samples of produced water may also be analyzed for a decrease in total dissolved solids (TDS) content (salinity) associated with breakthrough of the low salinity water into the production well(s) 1a-1d. The person skilled in the art will understand that for a secondary low salinity waterflood, after low salinity water breakthrough into the production well(s) 1a-1d, the produced water comprises a mixture of connate water (the water originally in place in the reservoir) and low salinity water. For a tertiary waterflood, after low salinity water breakthrough into the production well(s), the produced water typically comprises a mixture of: (a) connate water, (b) any previously injected water (for example, a high salinity water), and (c) the injected low salinity water. The produced water may be sampled either continuously or intermittently. Breakthrough of the bank of incremental oil may occur before breakthrough of the low salinity water into the injection well. However, owing to heterogeneities in the reservoir, for example, differences in permeabilities of the oil-bearing layers of the reservoir, there may be breakthrough of low salinity water into the production well(s) from one or more of the higher permeability oil-bearing layers before breakthrough of the bank of incremental oil from one or more of the lower permeability oil-bearing layers.

The information relating to breakthrough of low salinity water into the production well(s) together with the information relating to the presence of incremental oil in the oil produced from the production well(s) allows more effective management of the low salinity waterflood. Thus, the progression of the sweep of the low salinity waterflood can be easily identified by comparing samples of produced oil and optionally produced water taken over time at the one or more production wells (relative to baseline samples of oil and produced water). Proper steps can then be taken to control water cut, target by-passed oil if identified, and prolong well life.

Optionally, a tracer may be added to the low salinity injection water and the produced water is analyzed for the presence of tracer which is indicative of low salinity water break-through at the production well(s).

Where there is more than one production well, it is preferred that oil is sampled from each of the production wells and the samples of oil from each of the production wells are analyzed to establish post-flood composition signatures for the oxygen-containing organic compounds in the oil. Thus, the identification of the presence or absence of composition signatures for oxygen-containing organic compounds that are indicative of incremental oil in the various production wells allows the progress of the low salinity waterflood to be monitored, in particular, by identifying regions of the reservoir where incremental oil has not been produced. Where there is more than one injection well and a tracer is added to the low salinity injection water, it is preferred that a different tracer is used for each injection well thereby allowing movement of the low salinity injection water through the reservoir to be monitored (i.e. movement between different injection and production well pairs).

In addition, for a tertiary low salinity waterflood, the oil to water (o/w) ratio of the fluids produced from the production well(s) may be monitored by determining the total production rate for the produced fluids (oil, water and gas) and the production rates for the produced oil and water streams that are separated at the production facility. An increase in o/w ratio is indicative of a bank of incremental oil arriving at one or more of the production wells. If possible, the o/w ratio for each production well may be monitored by sampling the fluids removed from each production well.

The samples of produced oil may be analyzed at the production facility or may be analyzed in a laboratory remote from the production facility. Similarly, the samples of produced water may be analyzed at the production facility or may be analyzed in a laboratory remote from the production facility. In order to mitigate the risk of any changes to the chemical composition of the samples, the samples may be refrigerated prior to analysis (for example, may be cooled to a temperature of less than 10° C., in particular, a temperature in the range of 3 to 5° C.). The risk of any changes in the chemical composition of the samples may be further mitigated by ensuring that oxygen is excluded from the samples. In particular, the samples may be stored under an inert atmosphere, for example, under an atmosphere of nitrogen. Preferably, the samples of produced oil are stored for less than 1 month, more preferably, less than 2 weeks, in particular, less than 1 week before analysis.

As discussed above, the methods 200, 400 and 600 may be carried out during either a secondary or tertiary low salinity waterflood.

There may be one injection well and one production well, but preferably there may be more than one injection well and more than one production well. There may be many different spatial relationships between the, or each, injection well and the, or each, production well. Injection wells may be located around a production well. Alternatively the injection wells may be arranged in two or more rows between each of which are located production wells. Common injection patterns for land based fields are direct line drive, staggered line drive, two-spot, three-spot, four-spot, five-spot, seven-spot and nine-spot. The patterns are called normal or regular when they include only one production well per pattern. Patterns are described as inverted when they include only one injection well per pattern. The person skilled in the art will know how to operate the injection wells of a "pattern flood" to achieve maximum oil recovery during the low salinity waterflood.

The flood pattern may be altered over the period of operation of a reservoir to change the direction of flow in a reservoir with the intent of contacting unswept oil. It is also common to reduce the flood pattern size by infill drilling, which improves oil recovery by increasing reservoir continuity between injection wells and production wells. However, this is less feasible for offshore reservoirs owing to the high cost of infill drilling. The methods 200, 400 and 600 may be used to determine optimal locations for infill drilling on the basis of the presence or absence of a difference in the compositional signature for the oxygen-containing organic compounds in the oil produced from existing production wells (and the magnitude of any such difference).

The present invention will now be illustrated by reference to the following Examples.

EXPERIMENTAL

The following examples from experimental results are useful for showing how the compositional signature for the oxygen-containing organic compounds in the moveable oil vary before and during a waterflood. The change in signatures can be attributed to the production of incremental oil.

Coreflood Facility

Coreflood experiments were performed using coreflood facilities operated at non-reservoir conditions (referred to in the art as "reduced conditions") of a temperature of up to 75° C. and a pore pressure of 20 bar absolute with a higher confining pressure of up to 60 bar absolute). The coreflood facility employed dead fluids (oil and water having no dissolved gas at the conditions of the test).

Core Plug Preparation

Core plugs (samples of rock), nominally 3" long by 1.5" in diameter were used for the study. However, the person skilled in the art will understand that different sized core plugs may also be used. The core plugs were prepared either from sandstone cores taken from oil reservoirs (cores A, B, C, D, E and I) or from a block of outcrop rock (cores F, G and H). By "core" is meant a cylindrical section of a reservoir rock obtained by drilling into the rock with a core drill that comprises a rotatable annular cutting tool and a cylindrical core storage device. There may be significant heterogeneity in rock properties between different rock layers of the core.

The porosities, permeabilities to water ($K_w$) at 100% water saturation ($S_w=1$) and mineral compositions of the core samples are shown in Table 1. In the case of outcrop rock samples, the mineral compositions were average values determined from X-ray Diffraction (XRD) measurements made on a number of outcrop rock samples. For core samples C and E, the mineral compositions were estimated using an adjacent sample of rock to the core sample used in the coreflood study. XRD data were not available for Core sample D.

TABLE 1

Rock Analyses

| Plug Type | Porosity | Kw at Sw = 1 (milliDarcies, mD) | % Quartz | % Clay content | % other minerals |
|---|---|---|---|---|---|
| Core A - Plug 1 | 24.8% | 190.0 | 94.3% | 3.1% | 2.6% |
| Core A - Plug 2 | 23.8% | 36.0 | 83.1% | 6.9% | 10.0% |
| Core B - Plug 1 | 15.2% | 37.1 | 75.3% | 11.6% | 13.0% |
| Core B - Plug 2 | 15.1% | 41.8 | 87.1% | 6.5% | 6.3% |
| Core C - Plug 1 | 24.8% | 91.2 | 69.4% | 20.5% | 10.1% |
| Core C - Plug 2 | 14.7% | 7.1 | 83.0% | 8.4% | 8.6% |
| Core D - Plug 1 | 16.0% | 128.2 | | | |
| Core E - Plug 1 | 18.9% | 15.1 | 68.6% | 3.6% | 27.8% |
| Core D - Plug 2 | 16.7% | 170.0 | 93.2% | 5.4% | 1.4% |
| Core C - Plug 3 | 21.7% | 108.9 | 78.5% | 14.0% | 7.5% |
| Core C - Plug 4 | 24.7% | 101.2 | 78.5% | 14.0% | 7.5% |
| Core F - Plug 1 | 15.2% | 37.5 | 76.0% | 11.3% | 12.7% |
| Core G - Plug 1 | 29.4% | 948.2 | 85.0% | 10.9% | 4.1% |
| Core H - Plug 1 | 24.6% | 158.1 | 86.6% | 8.4% | 5.0% |

"Other minerals" in Table 1 refers to crystalline minerals other than quartz and clays including dolomite, calcite, feldspars, siderite, plagioclase, pyrite, halite, hematite, goethite, and barite.

Each core sample was first restored i.e. the sample was cleaned using miscible solvents (for example, methanol and toluene) such that the core sample was as close to being in a "water wet" condition as possible. This cleaning was continued until the effluent from the core sample was colourless. After cleaning, the core sample was placed into a hydrostatic coreholder and was saturated with a high salinity connate water. The composition of the connate water used in each Example is given in Table 4. After a throughput of approximately 10 pore volumes (PV) of the connate water, the core sample was removed from the hydrostatic coreholder and the initial water saturation was set up in the core sample using the procedure described below.

Acquisition of Initial Water Saturation ($S_{wi}$)

It is essential that each core sample had a representative initial water saturation ($S_{wi}$) value. The initial water saturation for the core sample was achieved by a porous plate de-saturation technique, using the strongly non-wetting gas, nitrogen. This technique is well known to the person skilled in the art and will not be discussed further here. Once the initial water saturation was acquired, the core sample was loaded into a hydrostatic core holder and saturated with a refined oil under back pressure. A dispersion test (discussed below) was then performed to determine the value of $S_{wi}$ acquired.

Ageing of Core Samples

The core sample was then loaded into a coreholder and slowly raised in pressure and temperature to the test conditions.

The refined oil was then miscibly displaced at the test conditions by a crude oil via a 0.5 PV slug of toluene. Thus, a slug of toluene was injected into the core sample before injecting the crude oil. The toluene is miscible with both the refined oil and the crude oil and therefore allows the refined oil to be readily displaced by the crude oil. After the differential pressure across the core sample had stabilized, effective permeability of the core sample to the crude oil was determined using a technique well known to the person skilled in the art. The core sample was then aged, at temperature, in the crude oil for either one week (Examples 1 to 8 and 10 to 13) or three weeks (Example 9). During the ageing period, the crude oil was replaced immediately before commencing waterflooding of the core sample. The crude oil was also replaced weekly during the ageing process for Example 9. A minimum of one Pore Volume of crude oil was injected into the core sample and a sufficient amount of crude oil was used to achieve a constant pressure drop (differential pressure) across the core sample.

The crude oils used in the ageing process have the properties shown in Table 2.

TABLE 2

| | Properties of Crude Oils | | | | |
|---|---|---|---|---|---|
| | Density at room | Viscosities | | Total Acid Number | Total Base Number |
| Crude Oil | temperature (g/mL) | at 40° C. (centistokes) | at 100° C. (centistokes) | (mg/g KOH) | (mg/g KOH) |
| 1 | 0.9155 | 40.5 | 6.8 | 0.42 | 0.39 |
| 2* | 0.9354 | 117.0 | 12.3 | 0.37 | 0.49 |
| 3 | 0.9171 | 41.7 | 6.8 | 0.23 | 0.52 |

*Crude oil 2 was diluted with dodecane to reduce its viscosity.

Coreflood Tests

All coreflood tests were performed under unsteady state conditions using procedures well known to the person skilled in the art.

Waters were injected into the core samples at the injection rates shown in Table 4 (which are typical frontal advance rates for a waterflood in a reservoir).

Secondary coreflood tests were performed using a single water (a low salinity water). The coreflood tests with the secondary low salinity waters were allowed to continue until the differential pressure and oil production readings reached equilibrium. In the context of oil production, equilibrium was taken to be reached when no oil was observed in the effluent that was removed from the core sample. Permeability of the core sample to water at residual (remaining) oil saturation was then measured using a technique well known to the person skilled in the art.

Tertiary coreflood tests were performed with a high salinity water in secondary recovery mode followed by a low salinity water in tertiary recovery mode. The waterflood with the secondary high salinity water was allowed to continue until the differential pressure and oil production readings reached equilibrium. The waterflood with the low salinity water was then commenced and was continued until the differential pressure, and oil production readings reached equilibrium. Again, in the context of oil production, equilibrium was taken to be reached when no oil was observed in the effluent removed from the core sample. Permeability of the core samples to water at residual (remaining) oil saturation was then measured. The compositions of the waters used in the coreflood tests are shown in Table 3.

TABLE 3

| | Water Compositions | | | | | | | | | |
|---|---|---|---|---|---|---|---|---|---|---|
| Salt | Water 1 mg/L | Water 2 mg/L | Water 3 mg/L | Water 4 mg/L | Water 5 mg/L | Water 6 mg/L | Water 7 mg/L | Water 8 mg/L | Water 9 mg/L | Water 10 mg/L |
| $NaHCO_3$ | 2464.43 | 74.48 | 191.37 | 6.28 | 191.37 | 6.28 | 191.37 | 31.90 | 0.00 | 47.84 |
| $Na_2SO_4$ | 0.00 | 0.00 | 0.00 | 0.00 | 0.00 | 0.00 | 0.00 | 0.00 | 0.00 | 0.00 |
| $CaCl_2 \cdot 2H_2O^a$ | 260.41 | 7.87 | 1467.07 | 48.12 | 1467.07 | 36.34 | 1467.07 | 9581.05 | 6700.00 | 5524.05 |
| $MgCl_2 \cdot 6H_2O^a$ | 276.03 | 8.34 | 10639.80 | 348.99 | 10639.80 | 163.60 | 10639.80 | 0.00 | 300.00 | 5319.90 |
| KCl | 68.64 | 2.07 | 724.57 | 23.77 | 724.57 | 23.77 | 724.57 | 724.57 | 600.00 | 724.57 |
| $SrCl_2 \cdot 6H_2O^a$ | 14.30 | 0.43 | 0.00 | 0.00 | 0.00 | 0.00 | 0.00 | 0.00 | 0.00 | 0.00 |
| NaI | 30223.25 | 913.35 | 0.00 | 0.00 | 0.00 | 0.00 | 50000.00 | 50000.00 | 28200.00 | 50000.00 |

TABLE 3-continued

| | Water Compositions | | | | | | | | | |
|---|---|---|---|---|---|---|---|---|---|---|
| Salt | Water 1 mg/L | Water 2 mg/L | Water 3 mg/L | Water 4 mg/L | Water 5 mg/L | Water 6 mg/L | Water 7 mg/L | Water 8 mg/L | Water 9 mg/L | Water 10 mg/L |
| NaCl | 0.00 | 0.00 | 23478.11 | 770.08 | 14086.87 | 462.04 | 3960.09 | 4093.80 | 0.00 | 4082.7 |
| TDS(mg/L) | 33090.87 | 1000.0 | 30489.72 | 1000.1 | 21098.48 | 596.22 | 60971.70 | 62085.16 | 33999.98 | 61520.39 |

[a]Water of crystallisation does not contribute to TDS.

TABLE 4

| | | | | Coreflood tests | | | |
|---|---|---|---|---|---|---|---|
| Example | Plug Type | Connate Water | Oil Type | Secondary Water | Tertiary Water 1 | Injection Rate (ml/hour) | Incremental Oil Recovered |
| 1 | Core A—Plug 1 | Water 1 | Oil 1 | Water 1 | Water 2 | 4 | Yes |
| 2 | Core A—Plug 2 | Water 1 | Oil 1 | Water 3 | Water 4 | 3.9 | Yes |
| 3 | Core B—Plug 1 | Water 7 | Oil 2 | Water 3 | Water 4 | 3.99 | Yes |
| 4 | Core B—Plug 2 | Water 7 | Oil 2 | Water 3 | Water 4 | 10 | Yes |
| 5 | Core C—Plug 1 | Water 3 | Oil 2 | Water 3 | Water 4 | 10 | Yes |
| 6 | Core C—Plug 2 | Water 7 | Oil 2 | Water 4 | | 4 | N/A |
| 7 | Core D—Plug 1 | Water 8 | Oil 2 | Water 3 | | 3.87 | |
| 8 | Core E—Plug 1 | Water 9 | Oil 2 | Water 3 | Water 4 | 3.86 | Yes |
| 9 | Core D—Plug 2 | Water 10 | Oil 3 | Water 3 | Water 6 | 3.82 | Yes |
| 10 | Core C—Plug 3 | Water 3 | Oil 3 | Water 3 | Water 4 | 10 | Yes |
| 11 | Core F—Plug 1 | Water 3 | Oil 3 | Water 4 | | 10 | N/A |
| 12 | Core G—Plug 1 | Water 3 | Oil 3 | Water 4 | | 10 | — |
| 13 | Core H—Plug 1 | Water 3 | Oil 3 | Water 4 | | 10 | N/A |

During the coreflood tests, samples of oil and produced aqueous effluent were collected and the amount of oil produced under different waterflood conditions was determined.

At the end of the sequence of waterfloods, the final oil saturation of the core sample was determined by means of a dispersion test (as described below) thereby ensuring effective mass balancing during the waterflooding sequence.

Dispersion Tests

Dispersion tests were used at different stages of the preparation of the core sample and the coreflood experiments. The objective of a dispersion test is to measure the volume of fluid within the core sample at different stages of the experiments. For example, a dispersion test carried out on a core sample that is at 100% water saturation will provide the pore volume and porosity of the core sample, a dispersion carried out on the core sample when at initial water saturation ($S_{wi}$) or at residual oil saturation ($S_{or}$) will provide a measure of these saturation values. Thus, the dispersion test results provide quality assurance for the volumetric data that are obtained during the coreflood experiments.

In a dispersion test, an undoped fluid located in the pore space of the core sample may be miscibly displaced by doped fluid or a doped fluid located in the pore space of the core sample may be miscibly displaced by an undoped fluid. Thus, an undoped aqueous fluid may be miscibly displaced by an 'iodide' doped aqueous fluid (or vice versa) while an undoped oleic fluid may be miscibly displaced by an 'iodo-decane' doped oleic fluid (or vice versa). The doped oleic fluid may be a doped refined oil. The density of the miscibly displaced fluid (effluent) is determined over time by taking samples of the effluent. The densities of the samples of effluent are normalized to the density of the doped fluid ($\rho_{sample} = \rho_{effluent}/\rho_{doped\ fluid}$) and the normalized densities are plotted against the volume of effluent displaced from the core when each of the samples of effluent were taken. The volume of the mobile fluid (aqueous or oleic fluid) within the core sample is then calculated from the volume of the displaced fluid present in the effluent samples. Thus, the volume of mobile fluid may be deduced from the densities and volumes of each of the effluent samples.

When a dispersion test is performed for a core sample at 100% water saturation, aqueous fluids are used and the test gives a value for the total pore volume of the core sample.

When a dispersion test is performed with a core sample at initial water saturation, $S_{wi}$, part of the pore volume of the core sample is occupied by a mobile oil phase, with the remainder of the pore volume occupied by an immobile water phase. The dispersion test therefore uses an iodode-cane doped oil (oleic fluid) as the displacement fluid. Accordingly, the volume of aqueous fluid in the pore space of the core sample at $S_{wi}$ is:

Volume of Aqueous Fluid=Total Pore Volume−Volume of oil.

When a dispersion test is performed with a core sample at residual oil saturation, $S_{or}$, part of the pore volume of the core sample is occupied by a mobile aqueous phase with the remainder of the pore space occupied by an immobile oil phase. The dispersion test therefore uses an iodide doped aqueous fluid. Accordingly, the volume of oil in the pore space of the core sample at $S_{or}$ is:

Volume of Oil=Total Pore Volume−Volume of Aqueous Fluid.

Thus, provided the total pore volume of the core sample has been determined, the volume of oil remaining in the core sample can be determined.

As discussed above, during the sequence of core floods, samples of produced oil and produced aqueous effluent were collected and the volume of oil produced under different waterflood conditions was determined.

Percentage incremental oil production was then calculated from:

$$[(S_{or}-S_{or}^1)/(S_{oi}-S_{or})] \times 100\%$$

With $S_{oi}$ (the initial oil saturation) being calculated from:

$$S_{oi}=(\text{hydrocarbon pore volume})/\text{total pore volume}.$$

Hydrocarbon pore volume was determined from dispersion tests carried out with the core sample at initial water saturation, $S_{wi}$. Total pore volume was determined from dispersion tests with all of the pore volume of the core sample filled with water i.e. before acquiring $S_{wi}$.

Residual oil saturation, $S_{or}$, was then calculated from the volume of oil produced during the secondary waterflood:

$$S_{or}=S_{oi}-[\text{oil produced from secondary waterflood}/\text{total pore volume}].$$

$S_{or}^1$ was determined using the volume of oil produced during the tertiary waterflood:

$$S_{or}^1=S_{or}-[\text{oil produced in the tertiary waterflood}/\text{total pore volume}].$$

The total amount of oil produced was compared with the final residual oil saturation of the cores, as determined from dispersion tests, to ensure effective mass balancing during the waterfloods.

In the tertiary low salinity coreflood tests, an increase in oil recovery of at least 1.5% over the preceding secondary high salinity coreflood test was taken to be indicative of incremental oil recovery.

High Resolution Mass Spectrometry

A number of oil samples from the coreflood experiments were selected for further analysis using High Resolution Mass Spectrometry (HRMS). These oil samples were diluted into an aromatic solvent such as toluene or xylene. Samples that were to be ionized using ESI(+) or ESI(−) techniques were then diluted into an alcohol. The oil samples from the coreflood experiments were analyzed using one or more of the following mass spectrometry instruments (analyzers): Fourier Transform-Ion Cyclotron Resonance-Mass Spectrometry (FT-ICR-MS), Liquid Chromatography-Time of Flight-Mass Spectrometry (LC-TOF-MS) and Ion Trap-Mass Spectrometry (IT-MS) instruments. HRMS is a powerful and versatile method for studying the detailed composition of crude oil. The HRMS techniques employed controlled ionization of components of the oil samples to generate organic ions and to minimize fragmentation of the organic ions. The ionization techniques employed were ESI(+), ESI(−), APPI(+) or APPI(−).

FT-ICR-MS, HR-TOF-MS and IT-MS measure the mass of ions very precisely which makes it possible to assign a unique elemental composition to each m/z value within manually set parameters. FT-ICR-MS used is a higher resolution technique than the HRTOF-MS and IT-MS used although all techniques have a resolving power (m/Δm) of about 100,000 or greater at 400 m/z.

It is possible to assign general formulae to classes of homologous compounds or a homologous series of compounds based on the assigned elemental compositions, the choice of ionization method and a detailed chemical analysis of the crude oil. In addition, the degree of unsaturation for each mass may be calculated from the assigned elemental composition, by determining a double bond equivalent (DBE) number, where a DBE of 1 corresponds to either one π bond (C═C or C═O bond) or one fully saturated closed ring. Representative chemical structures for organic compounds having DBE values of from 0 to 7 are shown in Table 5a and 5b. The person skilled in the art will understand that not all of the compounds shown in Tables 5a and 5b are found in crude oil and that crude oil may contain compounds having DBE values greater than 7.

TABLE 5a

Representative structures for double bond equivalents for Hydrocarbons and Oxygenates

| Double Bond Equivalent (DBE) | Hydrocarbons | Oxygenates |
|---|---|---|
| 0 | [structure] | [structure] |
| 1 | [structure] | [structure] |
| 2 | [structure] | [structure] |
| 4 | [structure] | [structure] |
| 7 | [structure] | [structure] |

TABLE 5b

Representative Structures for Double Bond Equivalents for Nitrogen Compounds and Sulfur Compounds

| Double Bond Equivalent (DBE) | Nitrogen Compounds | Sulfur Compounds |
|---|---|---|
| 0 | [structure] | [structure] |
| 1 | [structure] | [structure] |
| 2 | [structure] | [structure] |
| 4 | [structure] | [structure] |

TABLE 5b-continued

Representative Structures for Double Bond Equivalents for Nitrogen Compounds and Sulfur Compounds

| Double Bond Equivalent (DBE) | Nitrogen Compounds | Sulfur Compounds |
|---|---|---|
| 7 | quinoline structure | thiochromone structure |

The HRMS instruments used to analyze the selected oil samples were a 12 T Bruker SolariX Fourier transform ion cyclotron resonance mass spectrometer, a 4.7 T Bruker SolariX Fourier transform ion cyclotron resonance mass spectrometer, a LECO Citius HR-TOF mass spectrometer and a ThermoScientific Orbitrap™ IT mass spectrometer. For the FT-ICR mass spectrometer, samples were introduced by infusion, and between 200 and 300 spectra were averaged to give the total mass spectrum. For the HR-TOF and IT mass spectrometers, the samples were introduced either by infusion or by flow injection analysis (FIA) i.e. with the liquid chromatography column removed from the instrument. For the HR-TOF-MS technique, a smaller number of scans were averaged to form the mass spectrum than for the FT-ICR-MS technique, for example, less than 10. For the IT-MS technique, less than 10 scans were averaged when APPI was used as the ionization technique or about 40 scans were averaged when ESI was used as the ionization technique. The HRMS instruments were operated at the following resolutions:

FT-ICR-MS—a maximum resolution of greater than 200,000 m/$\Delta$m at 400 m/z;

HR-TOF-MS—a maximum resolution of about 100,000 m/$\Delta$m at 400 m/z; and

IT-MS—a maximum resolution of greater than 180,000 m/$\Delta$m at 400 m/z.

The molecular weight cut-off for mass spectra produced using FT-ICR-MS was typically in the range of 1400 to 1600, for example, about 1500 m/z. The molecular weight cut-off for mass spectra produced using HR-TOF-MS was typically in the range of 800 to 850 m/z. The molecular weight cut-off for mass spectra produced using IT-MS was typically in the range of 1000 to 2000 m/z.

Spectra were further processed to yield elemental compositions (within <5 ppm mass error). Ions were assigned in the mass spectra using one of two methods: 1) MS software was used to assign ions falling within the following parameter ranges: elemental numbers of C=0-100, H=0-200, N=0-4, O=0-5, and S=0-3; or 2) a spectrum list was obtained from the collected MS data and this list was inputted into specialist petroleomics software. Data were re-calibrated using this software and ions were assigned falling within the following parameter ranges: C=0-100, H=0-200, N=0-4, O=0-5, and S=0-3.

To further improve data interpretation, only elemental compositions assigned to a class of homologous compounds consisting of at least 3 members, for example, at least 5 members were used. The class of homologous compounds may be either a class of homologous hydrocarbon compounds or a class of homologous hydrocarbon compounds that contain one or more heteroatoms, for example, one or more heteroatoms selected from O, N, and S. Preferably, only elemental compositions assigned to a homologous series within a class of homologous compounds were used wherein the series was defined by a range of DBE values. The person skilled in the art will understand that the members of a class of compounds have the same general formula but may differ in their structure or in their functional groups. The person skilled in the art would also understand that a homologous series within a class of homologous compounds refers to a group of compounds that differ only by the number of $CH_2$ units in their main carbon chain. The person skilled in the art will also understand that there are many different classes of homologous compounds in crude oil.

The principal ionization methods employed to analyze the oil samples using mass spectrometry were:

Negative ion Electrospray Ionization, ESI(−), which is capable of ionizing species such as phenols, carboxylic acids, pyrroles and pyrollidines. The classes of homologous compounds that may be detected include $C_xH_yO$, $C_xH_yO_2$, $C_xH_yO_3$ and $C_xH_yN$ wherein x and y are integers.

Positive ion Electrospray Ionization, ESI(+), which is capable of ionizing species such as amines and pyridines. The classes of homologous compounds that may be detected include $C_xH_yN$, $C_xH_yNS$, $C_xH_ySO$, $C_xH_ySO_2$, $C_xH_ySO_3$ and $C_xH_yNO$ wherein x and y are integers.

Positive ion Atmospheric Pressure Photoionization, APPI(+), which is capable of ionizing aromatic hydrocarbons, phenols, pyrroles and pyridines, and sulfur containing hydrocarbons such as thiophenes. The classes of homologous compounds that may be detected include $C_xH_y$, $C_xH_yS$, $C_xH_yS_2$, $C_xH_yO$ and $C_xH_yN$ wherein x and y are integers.

Negative ion Atmospheric Pressure Photoionization, APPI(−), which is capable of ionizing aromatic hydrocarbons, phenols, pyrroles, acids and sulfur containing hydrocarbons. The classes of homologous compounds that may be detected include $C_xH_y$, $C_xH_yS$, $C_xH_yS_2$, $C_xH_yO$ $C_xH_yO_2$ and $C_xH_yN$ wherein x and y are integers.

Prior to ionization, the oil samples were further diluted to a concentration in the range of 0.1 to 1 mg/mL in a solvent or a mixture of solvents. Examples of solvents and solvent mixtures that may be used for the various ionization methods are given in Table 6 below:

TABLE 6

Solvents

| Ionization Method | Suitable Solvents or Solvent Mixtures |
|---|---|
| APPI(+) | toluene |
|  | xylene:toluene (6:4 by volume) |
| APPI(−) | toluene |
|  | xylene:toluene (6:4 by volume) |
| ESI(+) | toluene:propan-2-ol (1:2 by volume) + 1% by volume acetic acid (174 mM) |
|  | toluene:methanol (1:2 by volume) |
|  | toluene:methanol (6:4 by volume) + 0.1% by volume formic acid (26.0 mM) |
|  | xylene:methanol (6:4 by volume) + 0.1% by volume formic acid (26.0 mM) |
| ESI(−) | dichloromethane:methanol (1:2 by volume) |
|  | toluene:methanol (1:5 by volume) + 0.1% by volume ammonium hydroxide (8.5 mM) |
|  | toluene:methanol (6:4 by volume) + 0.1% by volume ammonium hydroxide (8.5 mM) |
|  | xylene:methanol (6:4 by volume) + 0.1% by volume ammonium hydroxide (8.5 mM) |

The intensities of peaks assigned to individual ions in the spectra (that are markers for the incremental oil released during the low salinity flood) were normalized to the summed intensity of an abundant and stable class of homologous compounds thereby compensating for any variations in intensities caused by fluctuations in the ionization method. The resulting normalized intensities are hereinafter referred to as "primary normalized intensity data".

Preferably, the stable class of homologous compounds used for the normalization has a specific DBE number and a specific hydrogen deficiency (HD) number (also referred to in the art as "index of hydrogen deficiency"). Hydrogen deficiency numbers for organic compounds can be readily calculated by the person skilled in the art. For example, the hydrogen deficiency numbers for benzene ($C_6H_6$) and cyclohexane ($C_6H_{12}$) are −6 and 0 respectively.

The class of homologous compounds used for the normalization should be present in all samples of oil produced from a core sample during an individual flood. The stability of the intensities of the chosen class of homologous compounds means that this class of homologous compounds does not serve as a marker for the incremental oil released during a low salinity flood. Normalization of the intensities of the peaks in the spectra allows a comparison of intensities in mass spectra performed on samples of oil produced from a core sample across each flood and a comparison of the abundance of different individual compounds, classes of homologous compounds or homologous series of compounds in the mass spectra for each of the oil samples. The classes of homologous compounds used for the primary normalization for the ionization methods used for each Example are shown in Table 7 below.

Normalization of the intensities of the individual peaks in the mass spectra was carried out using the following equation:

$$\text{Normalized Intensity} = \frac{\text{Total intensity of individual ion} \times 1000}{\text{Summed total intensity for the normalization series}}$$

The total intensity of the individual ion is multiplied by 1000 to make the numbers more manageable.

The total intensity of an individual ion is determined from the intensity of the peak assigned to the monoisotopic form of the individual ion i.e. the ion that contains only the principle or most abundant isotopes for each element of its molecular formula (for example, 1H, 12C, 14N, 16O or 32S isotopes). The total intensity of the individual ion is then calculated from the intensity of the monoisotopic ion by taking into account ions that contain one or more less abundant isotopes of H, C, N, O or S. The mass and abundance of these isotopes are given below:

|     | Mass        | Abundance |
|-----|-------------|-----------|
| 2H  | 2.014101778 | 0.000115  |
| 13C | 13.00335484 | 0.0107    |
| 15N | 15.0001089  | 0.00364   |
| 17O | 16.9991317  | 3.80E−04  |
| 18O | 17.999161   | 2.05E−03  |
| 33S | 32.97145876 | 0.0076    |
| 34S | 33.9678669  | 0.0429    |
| 36S | 35.96708076 | 2.00E−04  |

To calculate the total intensity for all isotopic forms of an individual ion from the intensity of a monoisotopic ion, the following calculation is performed:

Total intensity of an individual ion=monoisotopic intensity×(1+(2H abundancy×number of hydrogen atoms in the molecular ion)+(13C abundancy×number of carbon atoms in the molecular ion)+(15N abundancy×number of nitrogen atoms in the molecular ion)+(17O abundancy×number of oxygen atoms in the molecular ion)+(18O abundancy×number of oxygen atoms in the molecular ion)+(33S×number of sulphur atoms in the molecular ion)+(34S abundancy×number of sulphur atoms in the molecular ion)+(36S abundancy×number of sulphur atoms in the molecular ion).

For example, for a molecular ion of molecular formula $C_9H_8O_1$ having a monoisotopic intensity of 425.8, the total intensity of the molecular ion is determined as follows:

425.8×(1+(0.0107×9)+(0.000115×8)+(3.80$E$−04×1)+(2.05$E$−03×1)=469.10389

The summed total intensity for the normalization series is the sum of all total intensities of the individual ions in the homologous series (within the class of compounds) of the normalization series.

TABLE 7

Examples of Classes of Homologous Compounds used for Primary Normalization for Different Ionization Methods

| Example | ESI(+) Series used for normalization | HD | DBE | ESI(−) Series used for normalisation | HD | DBE | APPI(+) Series used for normalization | HD | DBE | APPI(−) Series used for normalisation | HD | DBE |
|---|---|---|---|---|---|---|---|---|---|---|---|---|
| 1  | $C_xH_yN$ | −21 | 12 |           |     |    | $C_xH_y$ Rad  | −16 | 9  |           |     |   |
| 2  | $C_xH_yN$ | −21 | 12 |           |     |    | $C_xH_yN$ Rad | −25 | 14 |           |     |   |
| 3  | $C_xH_yN$ | −17 | 10 | $C_xH_yN$ | −17 | 10 | $C_xH_y$ Rad  | −14 | 8  |           |     |   |
| 4  | $C_xH_yN$ | −17 | 10 | $C_xH_yN$ | −21 | 12 | $C_xH_y$ Rad  | −16 | 9  |           |     |   |
| 5  | $C_xH_yN$ | −11 | 7  | $C_xH_yN$ | −21 | 12 |               |     |    |           |     |   |
| 6  | $C_xH_yN$ | −13 | 8  | $C_xH_yN$ | −15 | 9  |               |     |    |           |     |   |
| 7  | $C_xH_yN$ | −13 | 8  | $C_xH_yN$ | −15 | 9  | $C_xH_y$ Rad  | −16 | 9  | $C_xH_y$ Rad | −16 | 9 |
| 8  | $C_xH_yN$ | −13 | 8  | $C_xH_yN$ | −21 | 12 | $C_xH_y$ Rad  | −16 | 9  | $C_xH_y$ Rad | −16 | 9 |
| 9  | $C_xH_yN$ | −13 | 8  | $C_xH_yN$ | −15 | 9  |               |     |    |           |     |   |
| 10 | $C_xH_yN$ | −13 | 8  | $C_xH_yN$ | −15 | 9  |               |     |    |           |     |   |
| 11 | $C_xH_yN$ | −13 | 8  | $C_xH_yN$ | −15 | 9  |               |     |    |           |     |   |

TABLE 7-continued

Examples of Classes of Homologous Compounds used for Primary Normalization for Different Ionization Methods

| | ESI(+) | | | ESI(−) | | | APPI(+) | | | APPI(−) | | |
|---|---|---|---|---|---|---|---|---|---|---|---|---|
| Example | Series used for normalization | HD | DBE | Series used for normalisation | HD | DBE | Series used for normalization | HD | DBE | Series used for normalisation | HD | DBE |
| 12 | $C_xH_yN$ | −13 | 8 | $C_xH_yN$ | −15 | 9 | | | | | | |
| 13 | $C_xH_yN$ | −13 | 8 | $C_xH_yN$ | −15 | 9 | | | | | | |

ESI(+) all molecular ions are protonated
ESI(−) all molecular ions are deprotonated
Rad molecular ions are radical ions The normalized intensities of the individual ions are then subjected to a further normalization ("secondary normalization") wherein the total intensity of a class of homologous compounds or homologous series of compounds is determined and multiplied by 1000 (to give a "summed total intensity". "Secondary normalized intensity data" are then obtained by determining the ratio of the summed total intensity for the class of homologous compounds or homologous series of compounds for samples of oil produced across a low salinity flood to the summed total intensity for the same class of homologous compounds or homologous series of compounds for a baseline sample of oil. Typically, for a secondary coreflood test, the baseline sample of oil is removed from the core sample, at or near the beginning of the coreflood test (i.e. is an oil sample that could not have interacted with the injected low salinity water). Typically, for a tertiary low salinity coreflood test, the baseline sample of oil is removed during the preceding secondary high salinity coreflood test. Typically, oil samples were selected for mass spectral analysis to investigate potential markers for incremental oil in the secondary or tertiary low salinity coreflood tests, across the time period when an increased amount of oil was observed in the effluent removed from the core sample. In a secondary coreflood test, this typically occurred after breakthrough of low salinity water (also referred to as low salinity water).

The normalized intensity data for Examples 1 to 13 are shown in Table 8 below.

Examples 1 and 2 involved secondary corefloods with high salinity Waters 1 and 3 respectively and tertiary corefloods with low salinity Waters 2 and 4 respectively. Only positive ion ESI-MS analysis was completed for the oil samples removed during these coreflood tests. A comparison of the averaged normalized intensity data for the $C_xH_yN$ class of homologous compounds for oil samples produced for the secondary and tertiary corefloods (i.e. across the entire coreflood test) showed that the average normalized intensities did not vary significantly which indicated that the $C_xH_yN$ class of homologous compounds does not serve as a marker for incremental oil produced during a tertiary low salinity waterflood.

Example 3 relates to a secondary coreflood with high salinity Water 3 and a tertiary coreflood with low salinity Water 4. In Example 3, positive ion ESI-MS analyses of oil samples removed during the secondary and tertiary corefloods showed that the CxHyN class of homologous compounds remained stable across the entire coreflood test. Negative ion ESI-MS analyses of the oil samples revealed a slight increase in the normalized intensity for CxHyO₂ class of homologous compounds for oil samples removed during the tertiary low salinity coreflood summed across all identified DBE values (when compared with oil samples removed during the secondary high salinity coreflood. Isolating the averaged normalized intensity data for the CxHyO₂ class of compounds with DBE values of 1, showed a larger increase in the normalized intensity for oil samples removed during the tertiary low salinity coreflood (when compared with oil samples removed during the secondary high salinity coreflood). The CxHyO₂ class of homologous compounds therefore serves as a marker for incremental oil released during the tertiary low salinity coreflood with Water 4.

Examples 4 and 5 were coreflood tests using the same waters as for Example 3. The same conclusions may be drawn as for Example 3, i.e., the CxHyN class of homologous compounds remain stable in the oil samples removed across the entire waterflood while there is an increase in the concentration of the CxHyO₂ class of homologous compounds (for all identified DBE values and for DBE=1) for the oil samples removed during the tertiary low salinity flood (when compared with oil sample removed during the secondary high salinity flood). Although the variance for the intensities of the CxHyN class of homologous compounds for Example 5 is higher than for Examples 1 to 4, the variance is significantly less than the variance in the intensities for the CxHyO₂ class of homologous compounds across all identified DBE values and for DBE=1.

Example 6 shows the normalized intensity data for a secondary low salinity water flood with Water 4. Averaged normalized intensity data were obtained by normalising to an oil sample produced early in the corefloods (i.e oil displaced from a portion of the core plug yet to be swept by the low salinity water). The normalized intensities for CxHyN class of homologous compounds identified using positive ion ESI-MS was 118.97, similar to the values obtained for oil samples removed during the tertiary low salinity corefloods of Examples 1 to 5. The normalized intensity for the CxHyO₂ class of homologous compounds identified using negative ion ESI-MS had an average value of 200.95 (across all DBE) and of 920.58 (for DBE=1), indicating that the CxHyO₂ class of homologous compounds also acts as a marker for incremental oil released during a secondary low salinity waterflood.

Example 7 shows the normalized intensity data for a secondary high salinity water flood with Water 3. Averaged normalized intensity data were obtained by normalising to an oil sample produced early in the corefloods (removed from a portion of the core that was yet to be swept by the high salinity water). As for the previous examples, the average normalized intensity for the CxHyN class of homologous compounds was about 100 (99.61). The average normalized intensities for the CxHyO₂ class of homologous compounds across all identified DBE values (121.14) and for DBE=1 (156.8), were significantly lower than observed for the secondary low salinity coreflood test of Example 6 which indicates that a high salinity water is not as effective as a low salinity water in releasing this class of homologous compounds.

Example 8 shows the normalized intensity data for a secondary coreflood test with Water 3 and a tertiary low salinity coreflood test with Water 4. This Example used the same waters as Example 5 and similar results were obtained.

Example 9 relates to a secondary coreflood with high salinity Water 3 and a tertiary coreflood with low salinity Water 6. It was found that the averaged normalized intensity of the CxHyN class of homologous compounds remained stable for oil samples removed across the entire coreflood test while there was a marked increase in the averaged normalized intensity of the $C_xH_yO_2$ class of homologous compounds for oil samples removed during the tertiary low salinity coreflood for all identified DBE values and for DBE=1 (compared with oil samples removed during the secondary high salinity coreflood).

Example 10 relates to a secondary coreflood with a high salinity water and a tertiary coreflood with a low salinity water (the same waters were used as for Example 5). It was found that the averaged normalized intensity of the CxHyN class of homologous compounds remained stable for oil samples removed across the entire coreflood while there was a marked increase in the averaged normalized intensity of the $CxHyO_2$ class of homologous compounds for oil samples removed during the tertiary low salinity coreflood for all identified DBE values and for DBE=1 (compared with oil samples removed during the secondary high salinity coreflood).

Examples 11 to 13 are similar to Example 6 (secondary low salinity corefloods with Water 4). The same conclusions may be drawn as for Example 6.

homologous compounds for samples of oil taken during coreflood Experiment 1. Dotsize and shade of grey both correspond to intensities of the signals. The plot for the oil sampled from the reservoir (Sample 0) is the baseline pattern for carbon number versus DBE for the $C_xH_yO_2$ class of homologous compounds. Sample 1 was removed during aging of the core sample and prior to any waterfloods. It can be seen that the oil during aging is significantly depleted in $C_xH_yO_2$ compounds with high DBE numbers. Sample 2 was produced during the secondary high salinity waterflood. It can be seen that the plot for Sample 2 resembles the plot for the oil sampled from the reservoir (Sample 0). Sample 3 was removed at low salinity water breakthrough during the tertiary low salinity waterflood and the plot for this sample shows that the oil is enriched in compounds with low DBE numbers. Sample 4 is of oil produced later during the tertiary low salinity waterflood and resembles the plot for oil sample 3 taken immediately after low salinity water breakthrough. The plot for Sample 4 indicates that additional $C_xH_yO_2$ homologous compounds have been released from the reservoir rock later in the low salinity waterflood.

HR-TOF-MS Data for Coreflood Experiment 3 (Using ESI (−) as the Ionisation Technique)

Figure 8:
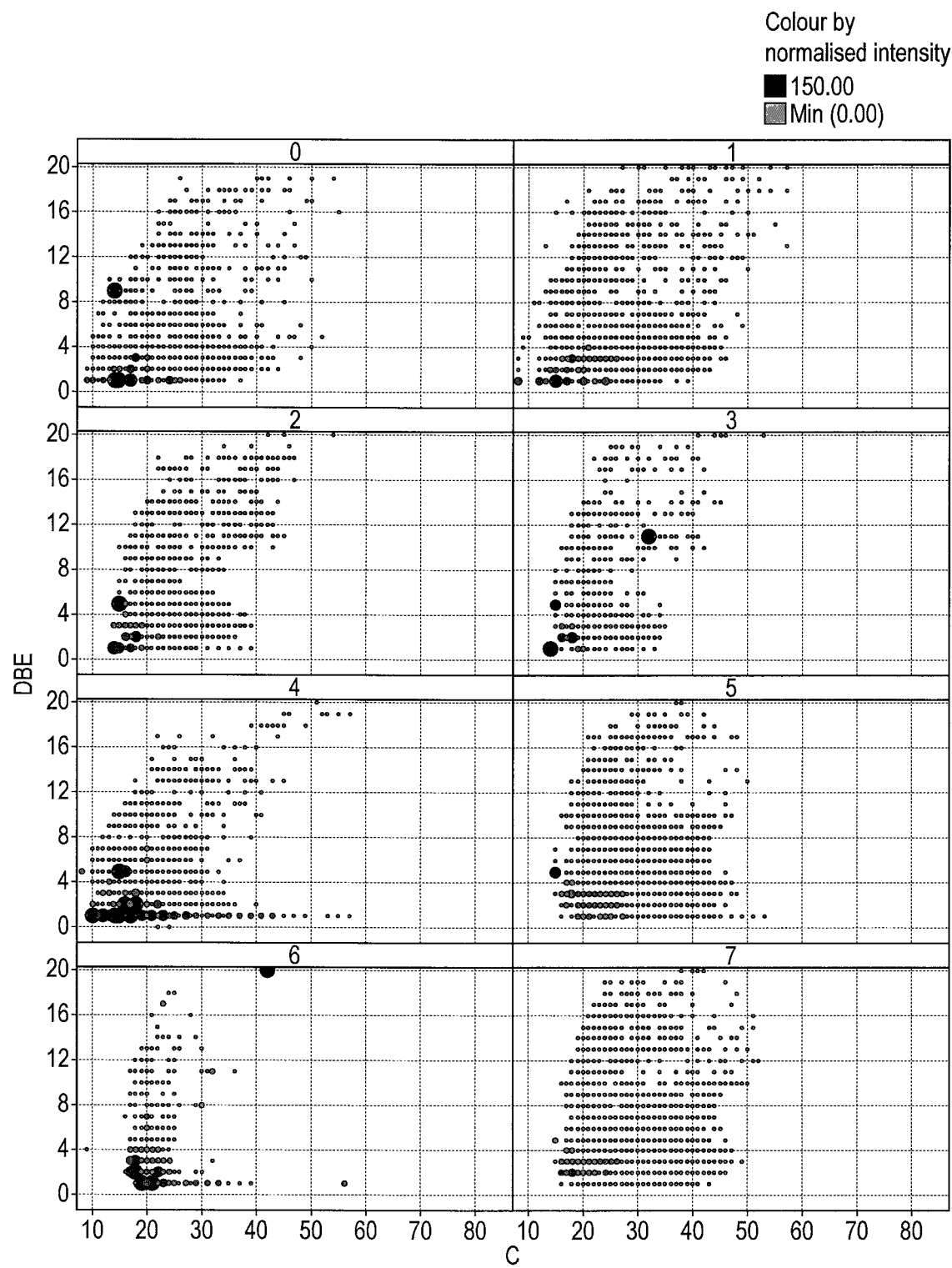
FIG. 8 is HR-TOF-MS data showing the carbon number (molecular size) versus Double Bond Equivalent (DBE) for the $C_xH_yO_2$ class of homologous compounds for samples of oil taken during a coreflood experiment (Example 3)

FIG. 8 shows the carbon number (molecular size) versus Double Bond Equivalent (DBE) values for the $C_xH_yO_2$ class of homologous compounds for samples of oil taken during coreflood Experiment 3. Again, dot size and shade of grey both correspond to the intensities of the signals. The data obtained using the LC-TOF-MS technique showed a similar pattern to the data obtained using the FT-ICR-MS technique.

Figure 9:
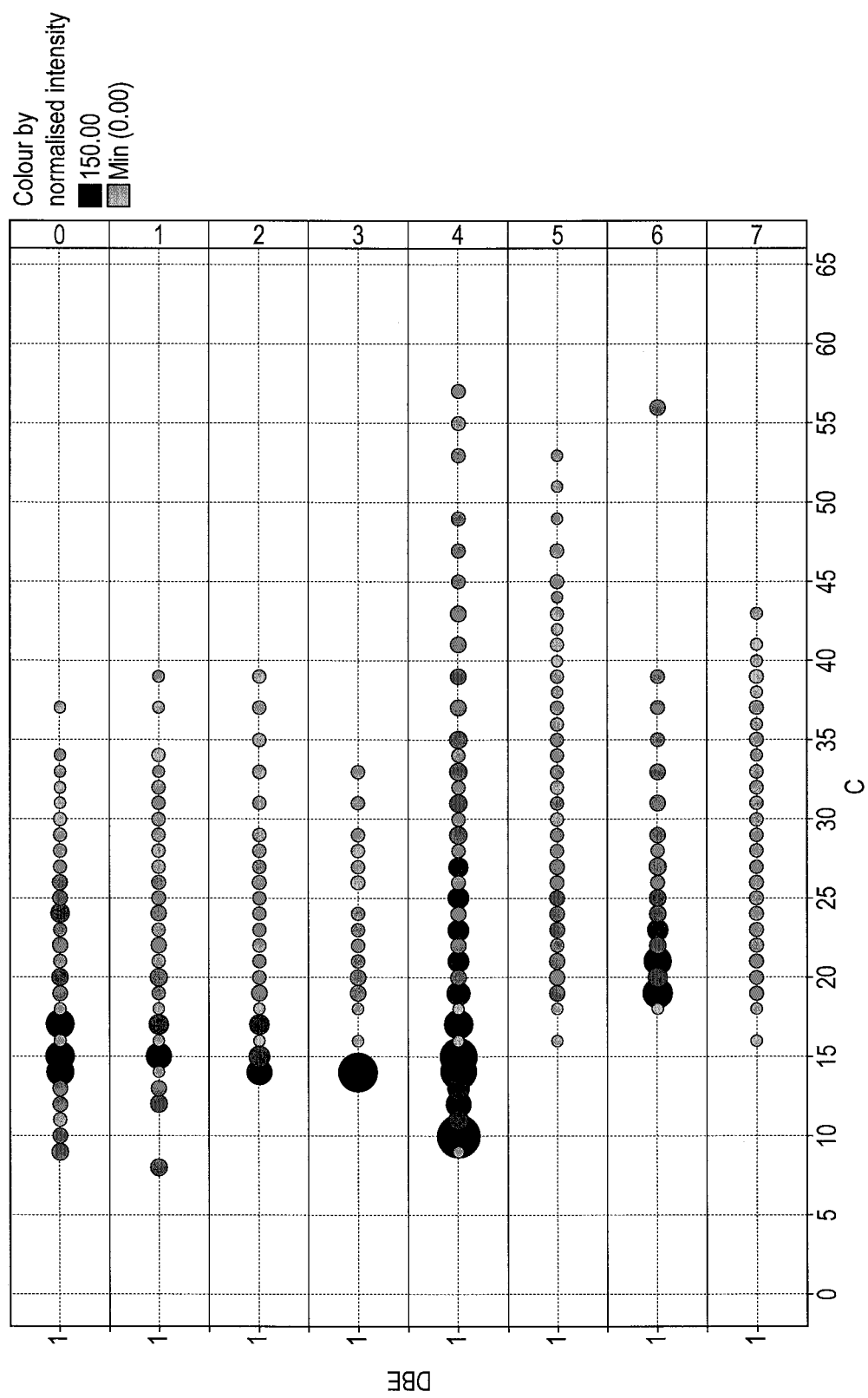
FIG. 9 is HR-TOF-MS data showing the carbon number (molecular size) for the $C_xH_yO_2$ class of homologous compounds with DBE values of 1.

FIG. 9 shows the carbon number (molecular size) for the $C_xH_yO_2$ class of homologous compounds with DBE values

TABLE 8

Secondary Normalized Intensities of Oil Samples

| | Average Normalised Intensities of Oil Samples | | | | | | Number of oil samples analyzed and intensities averaged | |
|---|---|---|---|---|---|---|---|---|
| | $C_xH_yN$ (ESI(+)) | | $C_xH_yO_2$ (ESI(−)) | | $C_xH_yO_2$ (ESI(−)) DBE = 1 | | | |
| Example | Secondary Coreflood Average | Tertiary Coreflood Average | Secondary Coreflood Average | Tertiary Coreflood Average | Secondary Coreflood Average | Tertiary Coreflood Average | During Secondary coreflood | During Tertiary Coreflood |
| 1 | 100 | 100.36 | — | — | — | — | 1 | 2 |
| 2 | 100 | 104.11 | — | — | — | — | 1 | 2 |
| 3 | 100 | 105.1 | 100 | 108.58 | 100 | 213.63 | 1 | 5 |
| 4 | 100 | 100.43 | 100 | 131.86 | 100 | 169.39 | 1 | 7 |
| 5 | 98.48 | 90.23 | 158.12 | 309.55 | 150.72 | 223.68 | 5 | 8 |
| 6 | 118.97 | — | 200.95 | — | 920.58 | — | 33 | |
| 7 | 99.61 | — | 121.14 | — | 156.8 | — | 6 | Not applicable |
| 8 | 104.01 | 130.81 | 95.22 | 171.53 | 99.05 | 373.64 | 5 | 15 |
| 9 | 96.24 | 106.34 | 289.52 | 359.65 | 426.21 | 972.05 | 7 | 18 |
| 10 | 103.09 | 111.26 | 99.43 | 171.86 | 191.73 | 505.12 | 3 | 8 |
| 11 | 98.68 | — | 149.62 | — | 162.28 | — | 18 | Not applicable |
| 12 | 101.04 | — | 124.73 | — | 140.06 | — | 24 | Not Applicable |
| 13 | 97.35 | — | 126.52 | — | 106.22 | — | 16 | Not Applicable |

FT-ICR-MS Data for Coreflood Experiment 3 (Using ESI(−) as the Ionisation Technique)

Example 3 was a tertiary low salinity coreflood test with Water 3 following a secondary coreflood test with a high salinity water (Water 4).

Figure 7:
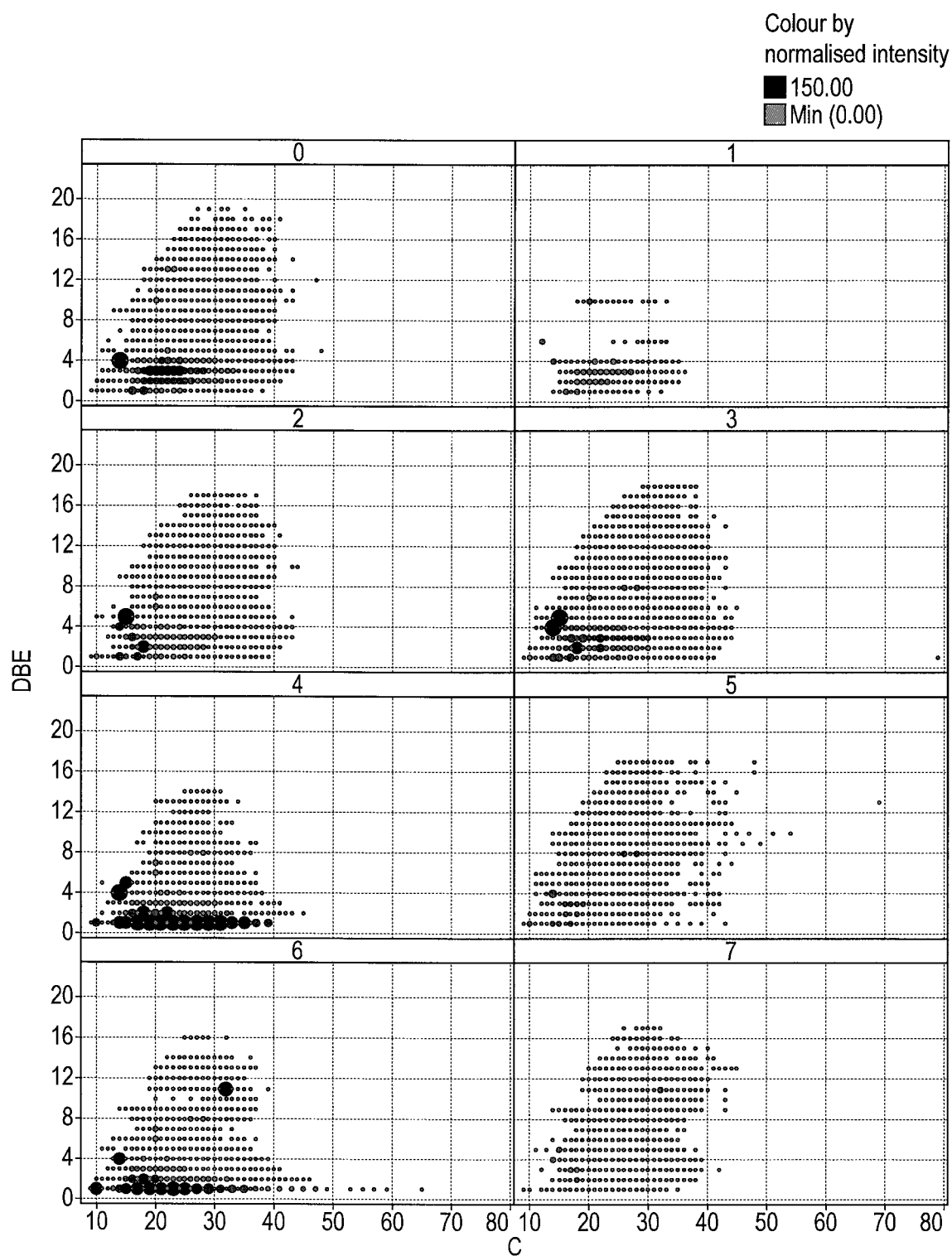
FIG. 7 is FT-ICR-MS data showing the carbon number (molecular size) versus Double Bond Equivalent (DBE) for the $C_xH_yO_2$ class of homologous compounds for samples of oil taken during a coreflood experiment (Example 3)

FIG. 7 shows the carbon number (molecular size) versus Double Bond Equivalent (DBE) for the $C_xH_yO_2$ class of of 1 for Samples 0, 1, 2, 3, 4, 5, 6 and 7. It can be seen that the Samples 4 and 6, taken after low salinity water breakthrough, are enriched in the $C_xH_yO_2$ class of homologous compounds (compared with baseline Sample 0). This indicates that the results obtained with FT-ICR-MS (see FIG. 7) are reproducible with the lower resolution LC-TOF-MS technique.

In conclusion, the results in Table 8 and FIGS. 7, 8 and 9 show that incremental oil can be detected by analyzing the samples of oil to establish post-flood compositional signatures for the oxygen-containing organic compounds in the oil. Incremental oil is said to be detected when an identified difference between one or more of the post-flood compositional signatures for the oxygen-containing organic compounds in the oil and the baseline compositional signature for the oxygen-containing organic compounds is found.

Furthermore, these results show that the differences can be observed for many types of core, oil and water.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method for detecting incremental oil production from an oil-bearing reservoir that is penetrated by at least one injection well and at least one production well, the process comprising:
    taking a baseline sample of the oil and analyzing the baseline sample of oil to establish a baseline compositional signature for the oxygen-containing organic compounds in the oil;
    commencing a low salinity waterflood by injecting a low salinity water into the reservoir from the injection well;
    recovering oil from the production well;
    taking post-flood samples of the oil produced from the production well over time;
    analyzing the post-flood samples of oil to establish post-flood compositional signatures for the oxygen-containing organic compounds in the oil; and
    identifying a difference between one or more of the post-flood compositional signatures for the oxygen-containing organic compounds in the oil and the baseline compositional signature for the oxygen-containing organic compounds in the oil that is characteristic of incremental oil released by the low salinity waterflood.

2. A method as claimed in claim 1, wherein the composition signatures for the post-flood samples of oil are compared with a baseline sample of moveable oil.

3. A method as claimed in claim 2, wherein the low salinity water is injected into the reservoir in secondary recovery mode.

4. A method for detecting incremental oil production from an oil-bearing reservoir comprised of a plurality of layers of reservoir rock wherein the reservoir is penetrated by at least one injection well, at least one production well and at least one surveillance well located between the injection well and production well, the process comprising:
    introducing logging equipment into the surveillance well;
    injecting a low salinity water into the reservoir from the injection well and recovering oil from the production well;
    utilizing the logging equipment over time to determine the period of time, $t_1$, between commencing injection of low salinity water into the reservoir from the injection well(s) and the detection of the front of the low salinity water at the surveillance well;
    determining the interwell distance, $L_1$, between the injection well(s) and surveillance well, and calculating the velocity, v, at which the front of the low salinity water advances through the reservoir, wherein $v=L_1/t_1$;
    determining the interwell distance, $L_2$, between the surveillance well and production well(s) and using the frontal advance velocity, v, to predict the time, $t_2$, at which the low salinity water breaks through into the production well, wherein $t_2=+L_2/v$;
    taking a baseline sample of oil from the reservoir and analyzing the baseline sample of oil to establish a baseline compositional signature for the oxygen-containing organic compounds in the oil;
    taking post-flood samples of the oil produced from the production well(s) over time and analyzing the samples of oil to establish post-flood compositional signatures for the oxygen-containing organic compounds in the oil to identify a difference between one or more of the post-flood compositional signatures for the oxygen-containing organic compounds in the oil and the baseline compositional signature for the oxygen-containing organic compounds in the oil that is characteristic of incremental oil released by the low salinity waterflood;
    increasing the frequency of at which post-flood samples of the produced oil are taken as the time approaches the predicted time, $t_2$, at which low salinity injection water breaks through into the production well and using the identified difference between the post-flood and baseline composition signatures for the oxygen-containing organic compounds in the oil to determine the time at which incremental oil breaks through into the production well.

5. A method as claimed in claim 4, wherein the samples of oil are analyzed using High Resolution Mass Spectrometry (HRMS) for an increase in the total signal intensity of the class of homologous compounds of general formula $C_xH_yO_n$ (I) wherein x is an integer in the range of 5 to 100, y is an integer$\leq 2x+2$, and n is an integer in the range of 1 to 10.

6. A method as claimed in claim 5, wherein the samples of oil are further analyzed using HRMS for a decrease in the intensity weighted double bond equivalent (DBE) value for the class of homologous compounds of general formula (I).

7. A method as claimed in claim 6, wherein the samples of oil are further analyzed using HRMS for an increase in the total signal intensity of the class of homologous compounds of general formula I having a Double Bond Equivalent (DBE) value of 1.

8. A method as claimed in claim 4, wherein samples of produced water taken after commencement of the low salinity waterflood are analyzed for an increase in the concentration of ions selected from $Fe^{2+}$, $Ca^{2+}$, $Mg^{2+}$ and $Sr^{2+}$ relative to a baseline sample of produced water taken before commencement of the low salinity waterflood.

9. A method as claimed in claim 8, wherein the samples of produced water are analyzed for a decrease in total dissolved solids content relative to a baseline sample of produced water taken before commencement of the low salinity waterflood.

10. A method as claimed in claim 4, comprising:
    recording the times at which each of the post-flood samples of oil are produced from the production well(s);
    determining the post-flood samples that show a difference between the post-flood compositional signature and the baseline compositional signature for the oxygen-containing organic compounds that is characteristic of incremental oil released by the low salinity waterflood, and taking the earliest production time at which a difference in compositional signature is detected in a post-flood sample as the breakthrough time for incremental oil into the production well(s).

11. A method of history matching a low salinity reservoir simulation to reservoir measurement data, the method comprising:

detecting incremental oil as claimed in claim 10, thereby to obtain the production time(s) at which incremental oil breaks through into the production well(s) as first reservoir measurement data;

obtaining further reservoir measurement data, the further reservoir measurement data comprising measured volume(s) of oil produced from the production well(s) during the low salinity waterflood, as a function of time;

inputting common input data and low salinity input data into the low salinity reservoir simulation to simulate the low salinity waterflood, wherein the common input data and the low salinity input data have associated uncertainties;

operating the low salinity reservoir simulation with the common input data and the low salinity input data to generate low salinity output data, the low salinity output data comprising:

the calculated time(s) at which incremental oil breaks through into the production well(s); and the calculated volume(s) of oil produced from the production well(s), under low salinity conditions, as a function of time; and generating a history matched reservoir simulator of the low salinity waterflood by history matching the low salinity output data to the reservoir measurement data by adjusting the uncertainties in the low salinity input data.

12. A method as claimed in claim 11, wherein the further reservoir measurement data additionally includes one or more of:

the measured volume(s) of low salinity water injected into the injection well(s) as a function of time;

the measured volume(s) of water produced from the production well(s) as a function of time;

the measured salinity of the produced water as a function of time;

the measured concentrations of selected ions in the produced water as a function of time; and the measured downhole pressures in the injection well(s) and production well(s) at the depth of the oil bearing layer(s) of the reservoir as a function of time.

13. A method as claimed in claim 11, wherein the history matched reservoir simulator is used in predictive mode to estimate future incremental oil production from the reservoir arising from the low salinity waterflood and/or to provide strategies for improved management of the low salinity waterflood in the reservoir.

14. A method as claimed in claim 11, wherein history matching of the reservoir simulation is repeated, one or more times, during the low salinity waterflood of the reservoir.

15. A method of estimating a volume of incremental oil produced from a reservoir, as a function of time, the method comprising:

history matching a low salinity reservoir simulation to reservoir measurement data as claimed in claim 11, wherein the generating a history matched reservoir simulator comprises adjusting the uncertainties in the common input data and in the low salinity input data;

inputting high salinity input data into the history matched reservoir simulator to simulate a high salinity waterflood;

operating the history matched reservoir simulator using common input data and the high salinity input data to generate high salinity output data, the high salinity output data including the calculated volume(s) of oil produced from the production well(s), under high salinity conditions, as a function of time; and estimating the volume of incremental oil by subtracting the calculated volume(s) of oil produced from the production well(s), as a function of time under high salinity conditions from the measured volume(s) of oil produced from production well(s) during the low salinity waterflood of the reservoir, as a function of time.

16. A method of estimating an extended period of dry oil recovery for a secondary low salinity waterflood, the method comprising:

estimating a volume of incremental oil produced from a reservoir, as a function of time, as claimed in claim 15, wherein the high salinity output data additionally includes the calculated time(s) at which the high salinity water breaks through into the production well(s); and estimating the extended period of dry oil recovery for the secondary low salinity waterflood by subtracting the calculated time(s) at which the high salinity water breaks through into the production well(s) from a measured time(s) at which the low salinity water breaks through into the production well(s).

17. A method of estimating an extended period of reduced water-cut for a tertiary low salinity waterflood, the method comprising:

estimating a volume of incremental oil produced from a reservoir, as a function of time, as claimed in claim 15, wherein the high salinity output data additionally includes the calculated water-cut(s) for the fluids produced from the production well(s); and estimating the extended period of reduced water-cut for the tertiary low salinity waterflood by subtracting the calculated water-cut(s) for the fluids produced from the production well(s) from a measured water-cut(s) for the fluids produced from the production well(s) during the tertiary low salinity waterflood.

* * * * *